(12) United States Patent
Iwamura et al.

(10) Patent No.: US 10,013,533 B2
(45) Date of Patent: Jul. 3, 2018

(54) PARALLEL PROCESSING CORONARY CIRCULATION SIMULATION METHOD AND SIMULATOR APPARATUS USING NEWTON-RAPHSON ANALYSIS

(71) Applicants: FUJITSU LIMITED, Kawasaki-shi, Kanagawa (JP); The University of Tokyo, Tokyo (JP)

(72) Inventors: Takashi Iwamura, Sagamihara (JP); Toshiaki Hisada, Tokyo (JP); Seiryo Sugiura, Tokyo (JP); Takumi Washio, Tokyo (JP); Junichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 13/874,904

(22) Filed: May 1, 2013

(65) Prior Publication Data
US 2013/0304445 A1 Nov. 14, 2013

(30) Foreign Application Priority Data
May 11, 2012 (JP) .................................. 2012-109067

(51) Int. Cl.
*G06F 19/00* (2018.01)
*G06F 17/50* (2006.01)
*G16H 50/50* (2018.01)

(52) U.S. Cl.
CPC ...... *G06F 19/3437* (2013.01); *G06F 17/5018* (2013.01); *G16H 50/50* (2018.01)

(58) Field of Classification Search
None
See application file for complete search history.

(56) References Cited

U.S. PATENT DOCUMENTS

2007/0001879 A1 1/2007 Kaftan et al.
2011/0085701 A1 4/2011 Kitamura
(Continued)

FOREIGN PATENT DOCUMENTS

JP 2007-44488 2/2007
JP 2010-220742 10/2010
(Continued)

OTHER PUBLICATIONS

Grinberg, "Large-Scale Simulation of the Human Arterial Tree," Clinical and Experimental Pharmacology and Physiology, vol. 36, p. 194-205, 2009.*
(Continued)

*Primary Examiner* — G. Steven Vanni
(74) *Attorney, Agent, or Firm* — Staas & Halsey LLP

(57) ABSTRACT

A geometric model of an organ represents its shape as a collection of elements formed from nodes and connections among them. A first vessel network model represents a network of first vessels whose diameters are larger than or equal to a threshold. A plurality of second vessel networks each represent a network of second vessels whose diameters are smaller than the threshold. In a simulator apparatus, a first analysis unit analyzes hemodynamics in the first vessels, based on the geometric model and first vessel network model of the organ and reflecting the motion of the organ. A second analysis unit analyzes hemodynamics in the second vessel network models connected to the nodes, by using output data of the first analysis unit which indicates the hemodynamics in the first vessels at each of the nodes.

6 Claims, 27 Drawing Sheets

(56) References Cited

U.S. PATENT DOCUMENTS

| | | |
|---|---|---|
| 2011/0135172 A1 | 6/2011 | Kitamura |
| 2013/0009958 A1 | 1/2013 | Kitamura |

FOREIGN PATENT DOCUMENTS

| | | |
|---|---|---|
| JP | 2011-98195 | 5/2011 |
| JP | 2011-212156 | 10/2011 |
| WO | WO 2013/071219 A1 | 5/2013 |

OTHER PUBLICATIONS

Kim, "Patient-Specific Modeling of Blood Flow and Pressure in Human Coronary Arteries," Annals of Biomedical Eng., vol. 38, p. 3195-3209, 2010.*

Ullah, "Numerical Simulation of Human Blood Flow in Microvessels," The Nucleus, vol. 46, No. 3, 4 pages, 2009.*

Smith, "An anatomically based model of transient coronary blood flow in the heart," SIAM Journal on Applied mathematics, vol. 62(3), p. 990-1018, 2002.*

Ghassan S.Kassab,et al., "Morphometry of pig coronary arterial trees", American Physiological Society Heart and Circulatory Physiology 265:pp. H350-H365, 1993.

Ghassan S.Kassab et al., "Morphometry of pig coronary venous system", American Physiological Society Heart and Circulatory Physiology 267:pp. H2100-H2113, 1994.

Ghassan S.Kassab et al., "Topology and dimensions of pig coronary capillary network", American Physiological Society Heart and Circulatory Physiology 267:pp. H319-H325, 1994.

Takumi Washio et al., "A Parallel Preconditioning for Heart-Coronary Circulation Coupling Simulation", JSCES Conference Proceedings, The Japan Society for Computational Engineering and Science (JSCES), vol. 14, May 2009.

Sonia Cortassa, et al. "A computational model Integrating Electrophysiology, Contraction, and Mitochondrial Bioenergetics in the Ventricular Myocyte", Biophysical Journal vol. 91, pp. 1564-1589, Aug. 2006.

N. Mittal et al., "Analysis of blood flow in the entire coronary arterial tree", American Journal of Physiology Heart and Circulatory Physiology 289:pp. H439-H446, Mar. 2005.

Dotan Algranati et al., "Mechanisms of myocardium-coronary vessel interaction", American Journal of Physiology Heart and Circulatory Physiology 298:pp. H861-H873, Dec. 2010.

W. J. Vankan et al., "Finite-element simulation of blood perfusion in muscle tissue during compression and sustained contraction", American Journal of Physiology Heart and Circulatory Physiology 273:pp. H1587-H1594, 1997.

C. C. van Donkelaar et al., "Spatial interaction between tissue pressure and skeletal muscle perfusion during contraction", Journal of Biomechanics vol. 34, Issue 5, pp. 631-637, 2001.

Smith et al, "A computational study of the interaction between coronary blood flow and myocardial mechanics", Physiological Measurement, vol. 25, No. 4, Aug. 2004, pp. 863-877.

Lassila et al, "Geometrical multiscale model of an idealized left ventricle with fluid-structure interaction effects coupled to a one-dimensional viscoelastic arterial network", Proceedings of the ECCOMAS Thematic International Conference on Simulation and Modeling of Biological Flows, Sep. 21-23, 2011, Brussels, Belgium pp. 1-9.

Extended European Search Report dated Mar. 23, 2016 in corresponding European Patent Application No. 13166112.6.

Extended European Search Report dated Dec. 11, 2014 in European Patent Application No. 14179666.4, 8 pages.

N. P. Smith et al., "Generation of an Anatomically Based Geometric Coronary Model," Annals of Biomedical Engineering, Biomedical Engineering Society, vol. 28, Jan. 2000, pp. 14-25.

B. Kaimovitz et al., "Large-Scale 3-D Geometric Reconstruction of the Porcine Coronary Arterial Vasculature Based on Detailed Anatomical Data," Annals of Biomedical Engineering, Biomedical Engineering Society, vol. 33, No. 11, Nov. 2005, pp. 1517-1535.

B. Kaimovitz et al., "A full 3-D reconstruction of the entire porcine coronary vasculature," American Journal of Physiology (Heart and Circulatory Physiology), American Physiology Society, vol. 299, Jul. 9, 2010, pp. H1064-H1076 with cover page.

C. D. Murray, "The physiological principle of minimum work. I. the Vascular System and the Cost of Blood Volume," Proceedings of the National Academy of Sciences, United States National Academy of Sciences, vol. 12, Mar. 1, 1926, pp. 207-214.

A. Kamiya et al., "Optimal Branching Structure of Vascular Tree", Seibutsu Butsuri (The Biophysical Society of Japan), vol. 13, No. 2, Mar. 1973 pp. 34-39 with cover page and 12 page translation.

R. Karch et al., "A three-dimensional model for arterial tree representation, generated by constrained constructive optimization," Computers in Biology and Medicine, Elsevier, vol. 29, Jan. 1999, pp. 19-38.

W. Schreiner et al., "Optimized arterial trees supplying hollow organs," Medical Engineering and Physics, Elsevier, vol. 28, Jun. 2006, pp. 416-429.

Z. L. Jiang et al., "Diameter-defined Strahler system and connectivity matrix of the pulmonary arterial tree," Journal of Applied Physiology, American Physiology Society, vol. 76, No. 2, Feb. 1994, pp. 882-892.

U.S. Appl. No. 14/447,799, filed Jul. 31, 2014, Takashi Iwamura, Fujitsu Limited.

Japanese Office Action dated Jan. 31, 2017 in related Japanese Application No. 2013-165855.

Japanese Office Action dated Jul. 4, 2017 in related Japanese Application No. 2013-165855.

Japanese Office Action dated Dec. 5, 2017 in related Japanese Application No. 2013-165855.

U.S. Office Action dated Jan. 25, 2018 in related U.S. Appl. No. 14/447,799.

* cited by examiner

41 BIFURCATED VESSEL MODEL

FIG. 12

310 FINITE ELEMENT MODEL

311 NODE DATA TABLE

| NODE NUMBER | COORDINATES |
|---|---|
| 1 | 0.00 0.00 0.00 |
| 2 | 0.00 0.00 0.50 |
| ⋮ | ⋮ |
| $N_{nodes}$ | 1.00 2.00 3.00 |

312 MESH DATA TABLE

| MESH NUMBER | NODE NUMBER |
|---|---|
| 1 | 1,2,3,4 |
| 2 | 2,3,4,5 |
| ⋮ | ⋮ |
| $N_{mesh}$ | $N_{nodes-2}$, $N_{nodes-1}$, $N_{nodes}$ |

FIG. 13

320 MACRO MODEL

321 NODE DATA TABLE

| NODE NUMBER | COORDINATES |
|---|---|
| 1 | 0.00 0.00 0.00 |
| 2 | 0.00 0.00 0.50 |
| ⋮ | ⋮ |
| $N_{nodes}$ | 1.00 2.00 3.00 |

322 VESSEL ELEMENT DATA TABLE

| ELEMENT NUMBER | NODE | LEVEL | RADIUS | CONDUCTANCE |
|---|---|---|---|---|
| 1 | 1,2 | 11 | 0.0015 | 7.6E-05 |
| 2 | 2,3 | 11 | 0.0014 | 7.0E-05 |
| ⋮ | ⋮ | ⋮ | ⋮ | ⋮ |
| $N_{elem}$ | $N_{nodes-1}, N_{nodes}$ | 6 | 0.0001 | 5.0E-11 |

FIG. 14

330 MICRO MODEL

331 NODE DATA TABLE

| NODE NUMBER | COORDINATES |
|---|---|
| 1 | 0.00 0.00 0.00 |
| 2 | 0.00 0.00 0.50 |
| ... | ... |
| $N_{nodes}$ | 1.00 2.00 3.00 |

332 VESSEL ELEMENT DATA TABLE

| ELEMENT NUMBER | NODE | LEVEL | LENGTH | DIAMETER | VESSEL WALL ELASTICITY | REFERENCE PRESSURE DIFFERENCE | QUANTITY |
|---|---|---|---|---|---|---|---|
| 1 | 1,2 | 5 | 4.5E-4 | 7.1E-5 | 9.7E-10 | 1.0E+4 | 1 |
| 2 | 2,3 | 4 | 1.12E-4 | 4.2E-5 | 4.6E-09 | 9.5E+4 | 8 |
| ... | ... | ... | ... | ... | ... | ... | ... |
| $N_{elem}$ | $N_{nodes-1}, N_{nodes}$ | 1 | 6.0E-5 | 6.5E-6 | 2.6E-09 | 3.0E+04 | 128 |

RELATIVE CAPILLARY DENSITY

PARALLEL PROCESSING CORONARY CIRCULATION SIMULATION METHOD AND SIMULATOR APPARATUS USING NEWTON-RAPHSON ANALYSIS

CROSS-REFERENCE TO RELATED APPLICATION

This application is based upon and claims the benefit of priority of the prior Japanese Patent Application No. 2012-109067, filed on May 11, 2012, the entire contents of which are incorporated herein by reference.

FIELD

The embodiments discussed herein relate to a simulation method and a simulator apparatus.

BACKGROUND

Recent advancement of measurement techniques in the biomedical field has enabled the researchers to make a considerable number of findings in proteins, cells, and organs. From the viewpoint of measurement, proteins, cells, and organs are distinct objects with different relative scales. One measurement technique is only applicable to the objects within a particular scale range, and so are the findings of the measurement. This means that the measurement-based approach is not capable enough for the researchers to make a satisfactory finding in the study field of, for example, interactive behavior of cells and organs. The difficulty comes from the large difference in scale between the cells and organs.

The computer technology, on the other hand, have evolved rapidly toward ever higher performance, and computer simulation takes advantage of such performance enhancements. Simulation-based research has been increasingly used to compensate for the lack of findings in the study that deals with objects in different scales (e.g., large objects in combination with small objects). This approach appears to be leading to new discoveries which could not have been achieved by the conventional measurement-based or experiment-based study.

Computer simulation is used in research of the heart, one of the most popular organs as a subject of study. The heart is an important organ that sends out blood to the entire body, where the blood circulation is one of the most fundamental mechanisms of life. It is noted that the heart itself also needs a stable supply of blood. Delivery of blood to the heart is done via a set of vessels known as the coronary circulatory system. Pathological conditions derived from abnormalities in the coronary circulation are collectively referred to as ischemic heart diseases.

Ischemic heart diseases are mainly caused as a result of coronary arteriosclerosis. Most studies about arteriosclerosis are made from the viewpoint of the biochemistry and cell biology. The pathogenesis of ischemic heart diseases is closely related to functional factors such as structure and control of the coronary circulatory system. For example, the heart contraction is considered to give a strong effect on the coronary blood flow. It is known that, with the presence of angina pectoris, ischemia is likely to occur at the endocardial (heart chamber) side of the heart wall, where the tissue pressure increases most significantly. The tissue pressure can be estimated by using a mechanics analysis tool. Observation of blood flow (shear stress) related to atheroma formation is also important in identifying the pathogenesis of ischemic heart diseases. The mechanics analysis also works well for this blood flow observation. As can be seen, the mechanics analysis plays an important role in study of the pathogenesis of ischemic heart diseases.

Such hemodynamics peculiar to the coronary circulation has drawn the interest of researchers including those who engaged in the basic medical sciences. They have made various kinds of experimental research and have accumulated many findings. There still remain, however, a lot of unknown things about the heart because of its complexity in structure and muscular motion. For example, the coronary system includes a wide range of vessels, from trunks to capillaries, on the order of mm to μm in diameter. That is, the largest coronary vessels are about 1,000 times as wide as the smallest coronary vessels. In addition, the heart repeats contraction and relaxation to make a large motion of strokes, which adds constraints to realtime observation of coronary blood vessels. These facts hamper the investigation of hemodynamics inside the heart wall. Computer simulation with a coronary circulation model is one way to overcome such technical difficulties in the physical observation of coronary vessels. This indeed is a powerful tool to illuminate the mechanisms of the heart.

Databases for coronary circulation simulation are available today to provide detailed measurement data about, for example, the diameter and length of coronary arteries, veins, and capillaries, as well as the information describing how the vessels branch out. With such databases, various simulation methods have been proposed and discussed as listed below. A coronary circulation simulation includes computation for solving simultaneous linear equations by using a parallel iterative method. For example, a preconditioner for parallel interactive sover is proposed to overcome the ill-conditioned problem caused by widely ranging vessel diameters in the coronary circulatory system and to ensure the convergence of iteration.

G. S. Kassab, C. A. Rider, N. J. Tang and Y. C. Fung, "Morphometry of Pig Coronary Arterial Trees," American Physiological Society Heart and Circulatory Physiology, 1993, 265: H350-H365.

G. S. Kassab, D. H. Lin and Y. C. Fung, "Morphometry of Pig Coronary Venous System," American Physiological Society Heart and Circulatory Physiology, 1994, 267: H2100-H2113.

G. S. Kassab and Y. C. Fung, "Topology and Dimensions of Pig Coronary Capillary Network," American Physiological Society Heart and Circulatory Physiology, 1994, 267: H319-H325.

Washio, Okada, Hisada, "A Parallel Preconditioning for Heart-Coronary Circulation Coupling Simulation," JSCES Conference Proceedings, The Japan Society for Computational Engineering and Science (JSCES), May 2009, Vol. 14

Cortassa S, Aon M A, O'Rourke B, Jacques R, Tseng H-J, Marban E, Winslow R L, "A computational model Integrating electrophysiology, contraction, and mitochondrial bioenergetics in the ventricular myocyte," Biophys J 91, pp. 1564-1589, 2006

The existing simulation techniques are, however, unable to analyze the dynamics of a circulatory system that not only involves a wide range of vessels, from coronary arteries and veins to capillaries, but also incorporates the motion of heartbeats. The main reason is that the modeling of capillaries, if done faithfully, would produce too large amount of data for the simulator to finish its job within a practical time. One way to circumvent the noted problem is to use a porous medium as a substitute for the capillary-level vessels. This conventional solution, however, sacrifices the ability to analyze the pressure drops in capillaries, effect of a microcirculation structure on the coronary blood flow, or interaction between metabolism and microcirculation. Here the term "metabolism" refers to a process in myocardial cells that consumes oxygen and nutrition delivered by the capillary blood flow to produce adenosine triphosphate (ATP) for energizing the cells.

The above-noted difficulties in the simulation of coronary circulation may also be true with other organs than the heart because their blood flow varies in synchronization with their motions. This means that the noted difficulties in the dynamics analysis of a circulatory system similarly apply to the conventional simulation of other organs because of the variety of vessels from trunks to capillaries and the effect of their motions on the vessels.

SUMMARY

According to an aspect of the embodiments to be discussed herein, there is provided a simulation method performed by a processor. This simulation method includes: storing a geometric model representing a shape of an organ as a collection of elements formed from a plurality of nodes and a plurality of connections among the nodes; storing a first vessel network model representing a network of first vessels whose diameters are larger than or equal to a specified threshold; storing a plurality of second vessel networks each representing a network of second vessels whose diameters are smaller than the specified threshold, wherein one or more of the second vessel networks are connected to each of the nodes; first analyzing, by a processor, hemodynamics in the first vessels belonging to the first vessel network model, based on the geometric model of the organ and reflecting motion of the organ; and second analyzing, by the processor, hemodynamics in the second vessels belonging to the second vessel network models connected to the plurality of nodes, by using result data of the first analyzing which indicates the hemodynamics in the first vessels at each of the nodes.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 12 illustrates an exemplary data structure of a finite element model;

FIG. 13 illustrates an exemplary data structure of a macro model;

FIG. 14 illustrates an exemplary data structure of a micro model;

DESCRIPTION OF EMBODIMENTS

Figure 1:
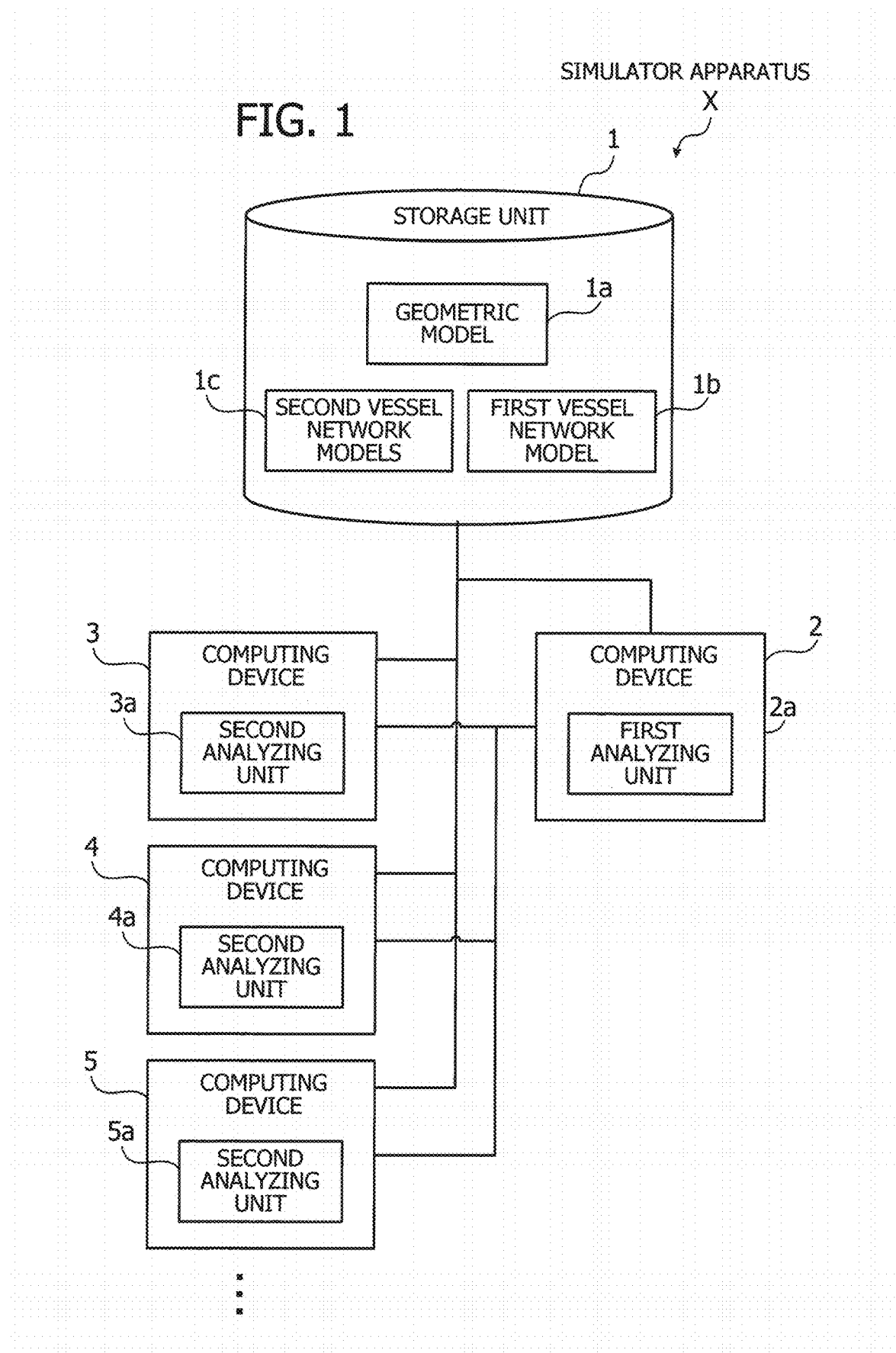
FIG. 1 illustrates an exemplary functional structure of a parallel computing system according to a first embodiment.

Several embodiments will be described below with reference to the accompanying drawings, wherein like reference numerals refer to like elements throughout. Each of those embodiments may be combined with other embodiments as long as there are no contradictions between them.

(A) First Embodiment

This section describes a simulation method according to a first embodiment, which improves the speed of computation relative to the conventional methods by applying a distributed processing scheme for a multi-scale analysis while taking advantage of anatomical features of organs under analysis. For example, the heart has an anatomical feature that there are no direct connections within the microcirculatory system, while the vessels are joined together only via some branches in their upstream or downstream portion. This anatomical feature of the heart may be utilized to improve the speed of simulation. Further, the first embodiment assumes symmetry of medium-scale vessels between microcirculatory vessels and large vessels. This assumption enables substantial reduction in the amount of computation.

FIG. 1 illustrates an exemplary functional structure of a parallel computing system according to the first embodiment. The illustrated simulator apparatus X includes a storage unit 1 and a plurality of computing devices 2, 3, 4, 5, and so on. This simulator apparatus X operates as a parallel computing system by executing concurrent processes on the computing devices 2, 3, 4, 5, . . . in parallel.

The storage unit 1 stores a geometric model 1a, a first vessel network model 1b, and a second vessel network model 1c. The geometric model 1a is a collection of geometric data that defines the shape of an organ as a plurality of elements (or interconnected nodes). The first vessel network model 1*b* is a collection of data that defines a network of intraorgan vessels whose diameters are greater than or equal to a specified threshold. The second vessel network model 1*c* is a collection of data that defines a network of intraorgan vessels whose diameters are smaller than the threshold. In the case of heart simulation, the first and second vessel network models 1*b* and 1*c* represent coronary circulation networks of the heart under analysis.

One computing device 2 includes a first analyzing unit 2*a*. Based on the geometric model 1*a* and first vessel network model 1*b*, the first analyzing unit 2*a* analyzes the condition of blood in the vessels of the first vessel network model 1*b*. The result data of this analysis indicates blood pressure and other properties at a plurality of nodes of the geometric model 1*a*. The organ under analysis may move as in the heartbeat caused by myocardial contraction and relaxation. Such motion of the organ could directly affect the second vessel network model 1*c*. The first analyzing unit 2*a* analyzes the state of several physical quantities such as pressure at each node by, for example, combining a blood flow analysis and an organic motion analysis of the first vessel network model 1*b*.

The above-described first analyzing unit 2*a* is employed in one computing device 2, while the other computing devices 3, 4, 5, . . . include second analyzing units 3*a*, 4*a*, 5*a*, . . . , respectively. With the information on hemodynamics at a plurality of nodes, the second analyzing units 3*a*, 4*a*, 5*a*, . . . analyze the hemodynamics in the second vessel network models 1*c* coupled to those nodes. For example, one or more second vessel network models 1*c* are coupled to each node of the geometric model 1*a*, and these second vessel network models 1*c* are assigned to the second analyzing units 3*a*, 4*a*, 5*a*, distributedly. The second analyzing units 3*a*, 4*a*, 5*a*, . . . analyze the hemodynamics in their assigned second vessel network models 1*c* by using data of pressure at each node of those second vessel networks models 1*c*. In this way, many computing devices 3, 4, 5, . . . operate in parallel to analyze the hemodynamics in a plurality of micro models.

The above computing devices 2, 3, 4, 5, . . . may each be implemented as a central processing unit (CPU) in the simulator apparatus X. These CPUs may be multi-core CPUs, in which case the individual cores in each CPU may serve as the computing devices discussed above. The storage unit 1, on the other hand, may be implemented as part of random access memory (RAM), hard disk drives (HDD), or other storage media in the simulator apparatus X.

It is noted that the lines interconnecting the functional blocks in FIG. 1 are only an example. FIG. 1 omits some communication paths for simplicity purposes. The person skilled in the art would appreciate that there may be other communication paths in the actual implementations.

The following section will describe in detail how the above simulator apparatus X of the first embodiment works in a coronary circulation simulation as an example of hemodynamics simulation. In this context, the description uses the terms "macro model" and "micro model" to refer to the first vessel network model 1*b* and second vessel network model 1*c*, respectively. It is also assumed that the second analyzing units 3*a*, 4*a*, 5*a*, analyze hemodynamics in micro models by using data about node pressures. The description uses the term "pressure node" to refer to a node to which a micro model(s) is coupled. More special terms are defined below.

Figure 2:
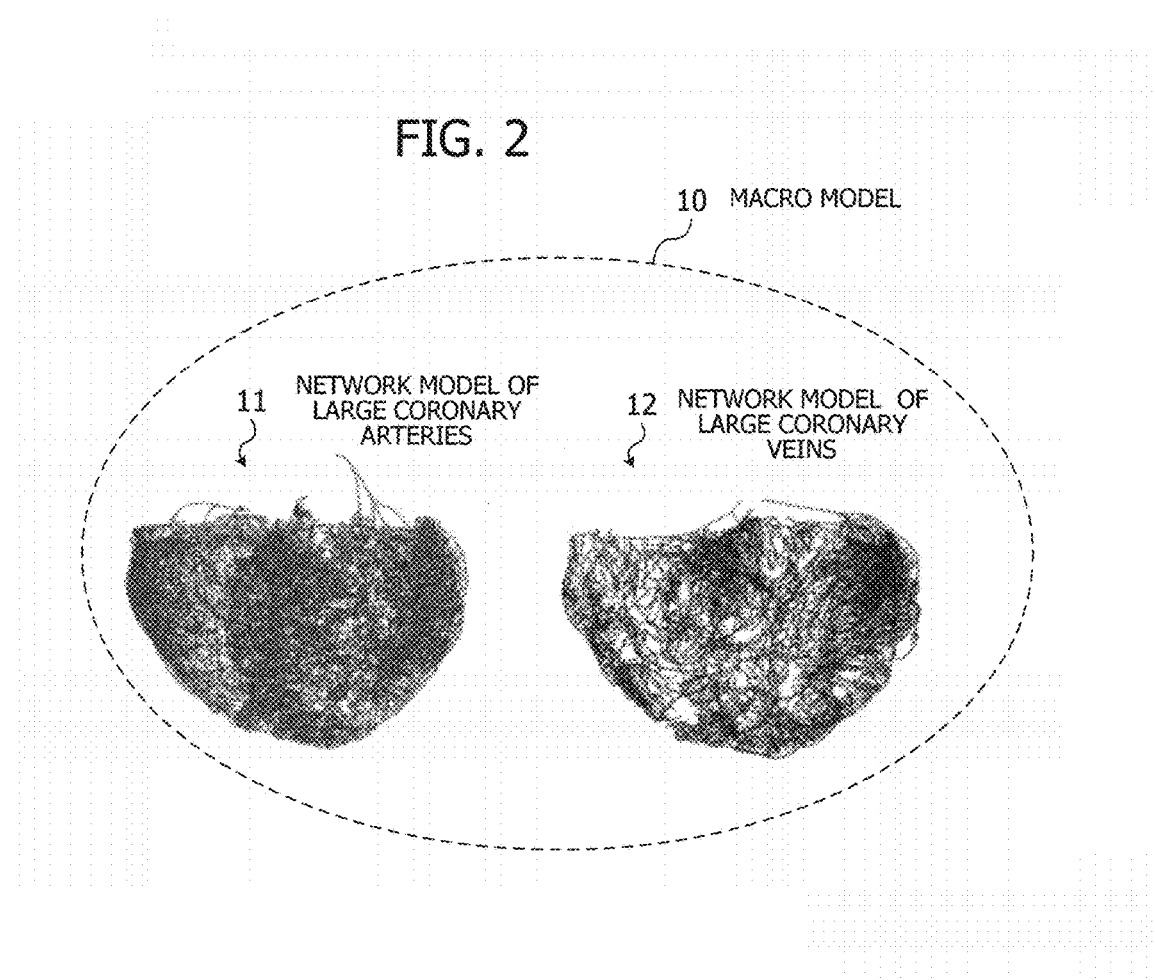
FIG. 2 illustrates an example of vessel network models representing large coronary arteries and veins.
Figure 3:
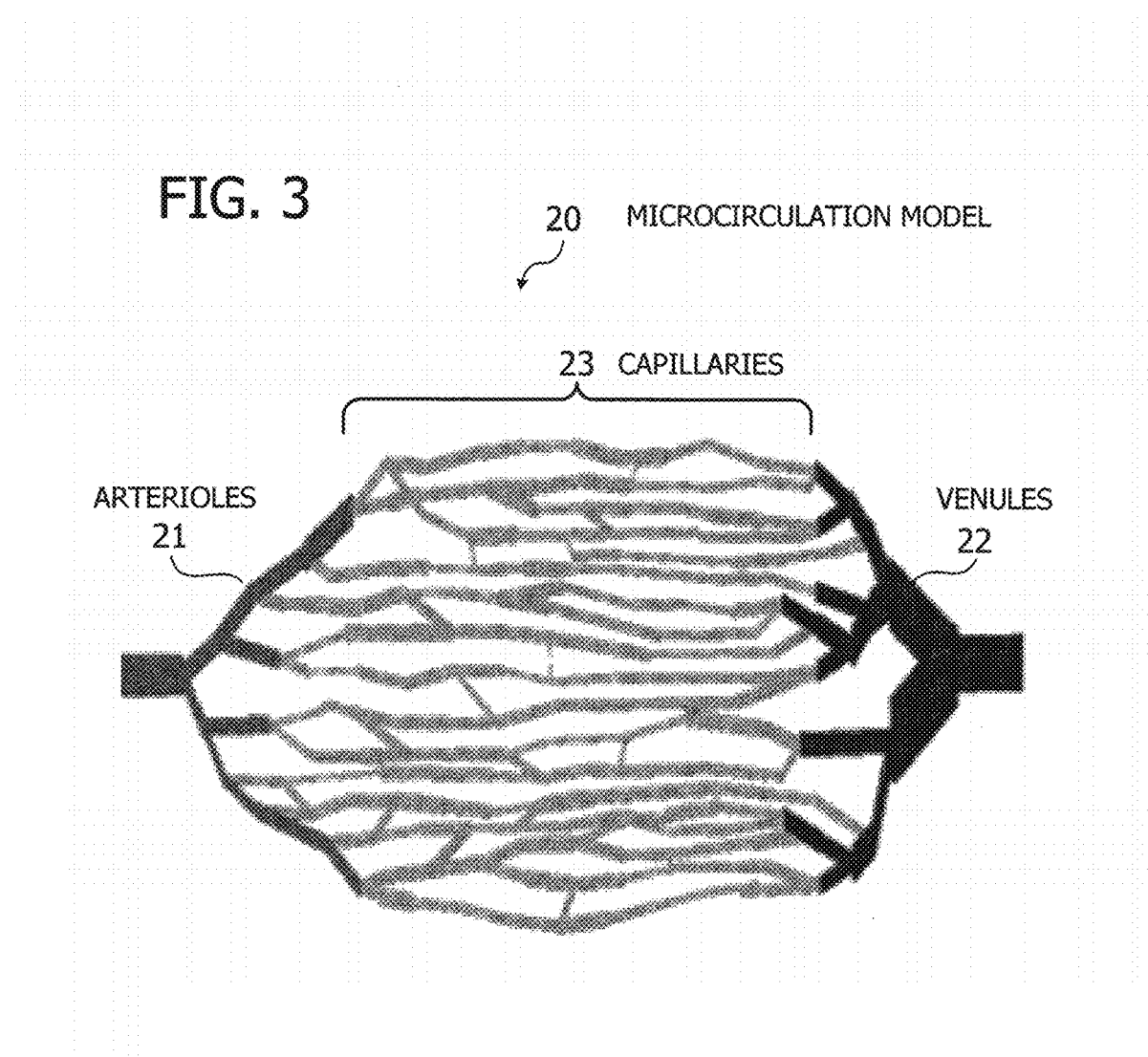
FIG. 3 illustrates an example of a microcirculation model.
Figure 4:
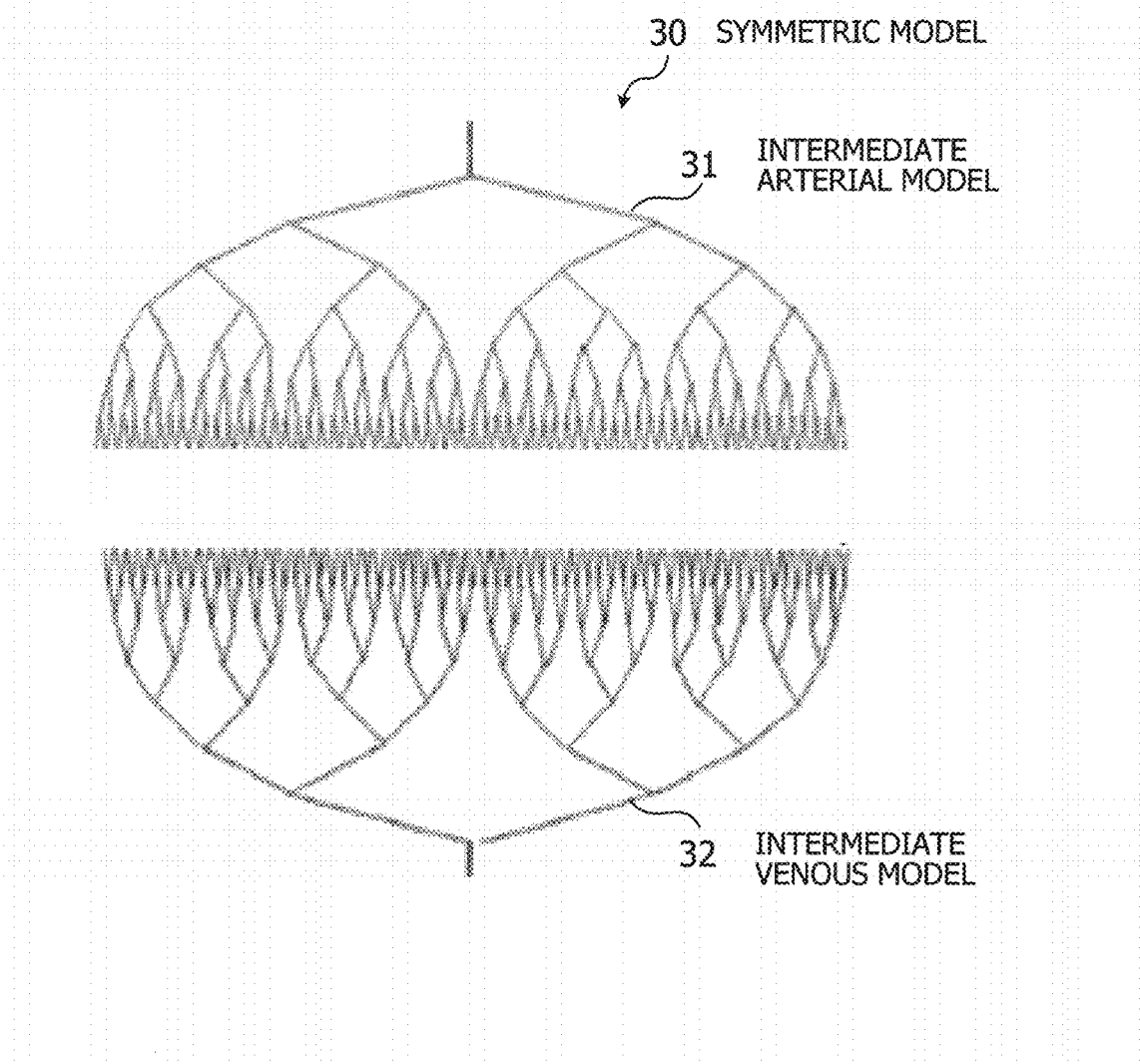
FIG. 4 illustrates an example of a symmetrical model.

(a) Terms large coronary artery, large coronary vein: vessels whose diameter is greater than about 100 µm (see FIG. 2)

medium scale vessels: vessels whose diameters are in the range of about 20 to 100 µm (see FIG. 4)

arteriole, venule: small vessels whose diameters are in the range of about 10 to 20 µm (see FIG. 3)

capillary: a minute vessel with a diameter of about 5 to 7 µm, whose wall acts as a membrane for interchange of oxygen and various nutrients between the blood and myocardial cells (see FIG. 3)

microcirculatory system: a system formed from arterioles, capillaries, and venules for delivering oxygen and various nutrients to myocardial cells (see FIG. 3)

(b) Multi-Scale Vessel Network Modeling

The first embodiment deals with blood vessel networks in every scale, from large coronary arteries and veins to capillaries. In this multi-scale blood vessel network, several large coronary arteries originate from the aorta and branch out into smaller arteries, then into arterioles, and finally into capillaries. The capillaries join and widen to become venules and then to become veins. These veins further join together to form large coronary veins and finally reach the right atrium of the heart. Suppose that, at each branching point of vessels, a larger vessel branch out into smaller vessels. The term "upper-scale vessel" will now be used to refer to the larger vessel. The term "lower-scale vessel" will be used to refer to the smaller vessels.

The process of modeling such a blood vessel network begins with producing two separate network models, one for large coronary arteries and the other for large coronary veins. FIG. 2 illustrates an example of vessel network models representing large coronary arteries and veins. Seen in the left half of FIG. 2 is a network model 11 of large coronary arteries, and seen in the right half is a network model 12 of large coronary veins. These two network models 11 and 12 then form a macro model 10.

The modeling process also provides a microcirculation model on the basis of anatomical data to represent a microcirculatory system including arterioles, venules and capillaries. FIG. 3 illustrates an example of such a microcirculation model. The illustrated microcirculation model 20 of FIG. 3 includes two sets of blood vessel networks, one for arterioles 21 (left) and the other for venules 22 (right). These two sets of vessels are interconnected by yet another blood vessel network made up of capillaries 23.

The modeling process further produces more vessel network models of a medium scale to provide connections between the above microcirculation model 20 and macro model 10. One such blood vessel network model belongs to the arterial system, and the other belongs to the venous system. It is assumed in the first embodiment that these two intermediate vessel networks are in symmetry with each other. Because of this assumption, the term "symmetric model" is used to refer to a pair of such vessel network models lying between a macro model and a microcirculation model.

FIG. 4 illustrates an example of a symmetrical model. The illustrated symmetric model 30 includes an intermediate arterial model 31 and an intermediate venous model 32, located on opposite sides of the capillaries. As seen from FIG. 4, the intermediate venous model 32 is a mirror image of the intermediate arterial model 31. In other words, these two intermediate models are similar to each other in the way of bifurcation of upper-scale vessels into lower-scale vessels, as well as in the diameters and lengths of such branching vessels. The assumption of symmetry enables drastic reduction of computational load, without losing inherent characteristics of the blood vessel networks.

The upper-scale ends of the produced symmetric model 30 are coupled to the macro model 10, while the lower-scale ends of the same are coupled to the microcirculation models 20. The symmetric model 30 and microcirculation models 20 form a vessel network model called a "micro model."

Figure 5:
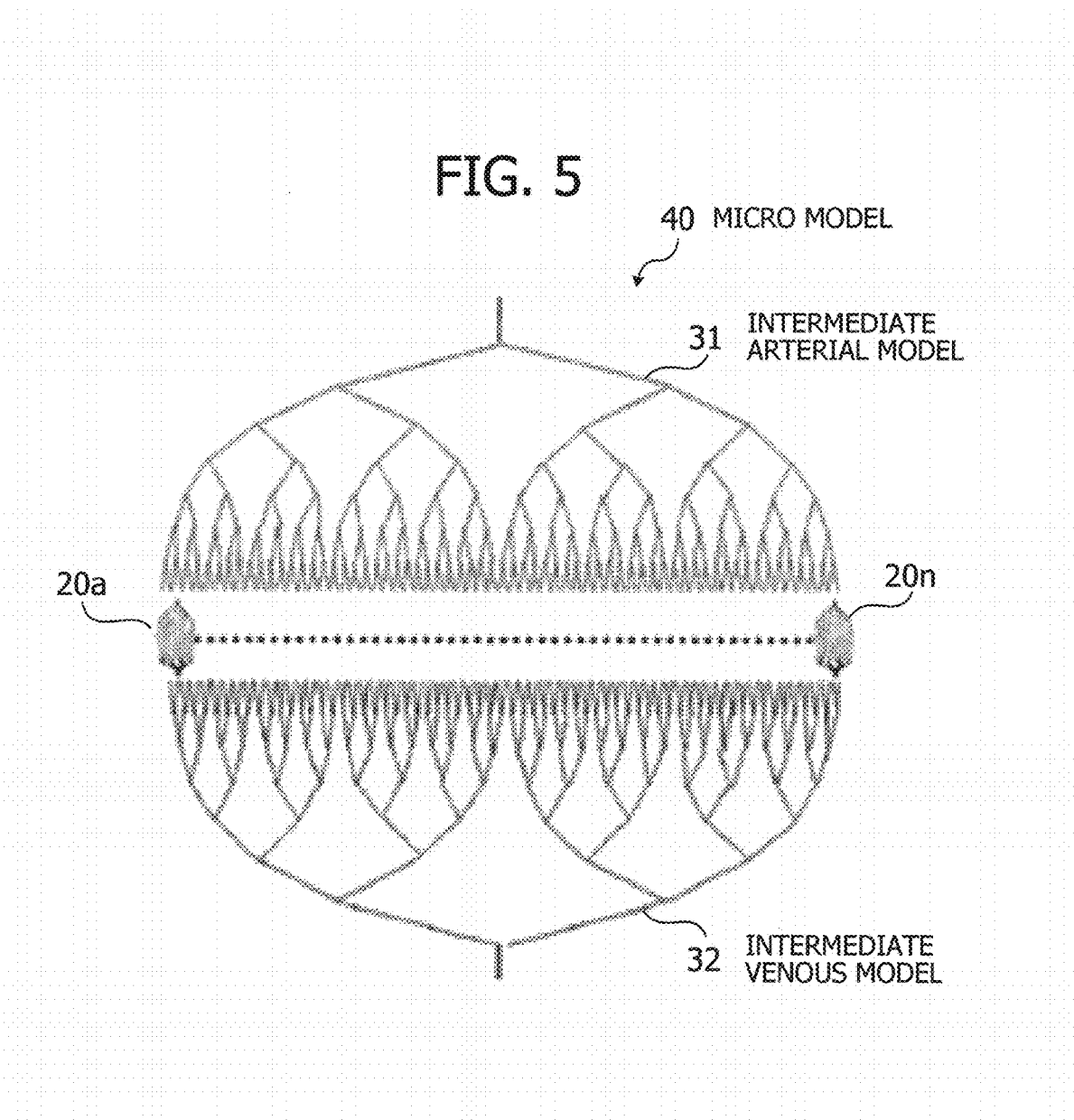
FIG. 5 illustrates an example of a micro model.

FIG. 5 illustrates an example of a micro model. The illustrated micro model 40 includes an intermediate arterial model 31, an intermediate venous model 32, and a plurality of microcirculation models 20a, . . . , 20n.

The modeling process now joins the macro model 10 and micro model 40 together, assuming that they virtually meet at the same points as pressure nodes k of the cardiac muscle. Pressure nodes k are vertices of each polyhedral element constituting a finite element model of the heart. The micro model 40 receives an external pressure from the cardiac muscle at each pressure node k, which is referred to as a myocardial node pressure $P_k$.

The number of micro models 40 coupled to a pressure node k is determined from lumped myocardial node volume $V_k^{muscle}$ of that pressure node. That is, the volume of each element is distributed to the pressure nodes that constitute the element. The term "lumped myocardial node volume" or $V_k^{muscle}$ refers to the sum of those distributed volumes at a specific pressure node k. For example, the elements may be tetrahedrons, each having four pressure nodes. In this case, the volume of one tetrahedron element is divided into four parts, and the divided volumes are each assigned to the four pressure nodes as their lumped myocardial node volumes $V_k^{muscle}$. One pressure node k may be shared by m elements, where m is an integer greater than zero. Then the lumped myocardial node volume $V_k^{muscle}$ at that node k is calculated by adding up the contributions of volume from those m elements.

The heart is known to have a higher density of blood vessels inside than outside. Specifically, the density of small vessels per myocardial volume varies depending on the transmurality (i.e., depth from the outer wall of the heart). Based on this anatomical feature of the heart, the modeling process takes the transmural difference into consideration when determining how many micro models 40 to connect to a pressure nodes k. For example, the lumped myocardial node volume $V_k^{muscle}$ of a pressure node is to be multiplied by a relative vessel density that reflects the transmurality of the node. More specifically, the relative vessel density increases as the pressure node is closer to the inside of the heart.

The modeling process then calculates a micro model vessel capacity $\rho_k$ representing the capacity of blood vessels contained in a unit volume at each pressure node. This calculation is performed on the basis of the ratio of total volume of vessels in the micro models to the myocardial volume. Let $V^{micro}$ be the total capacity of blood vessels in a single micro model. Then the following equation gives the number $n_k$ of micro models connected to a pressure node k at an extreme end point of the macro model.

$$n_k = \frac{V_k^{muscle} \rho_k}{V^{micro}} \quad (1)$$

Now that the number $n_k$ of connected micro models is determined for each of the pressure nodes, the following flow rate conservation law applies to each junction of arterial vessels and venous vessels in the macro model and micro models.

$$Q_{macro}^{\gamma} + n_k Q_{micro}^{\gamma} = 0 \quad (2)$$

where $Q_{macro}^{\gamma}$ represents the flow rate of blood sent out from a macro model to micro models, $Q_{micro}^{\gamma}$ represents the flow rate of blood sent out from a micro model to a macro model, and γ is a symbol for distinguishing arterial vessels from venous vessels.

Figure 6:
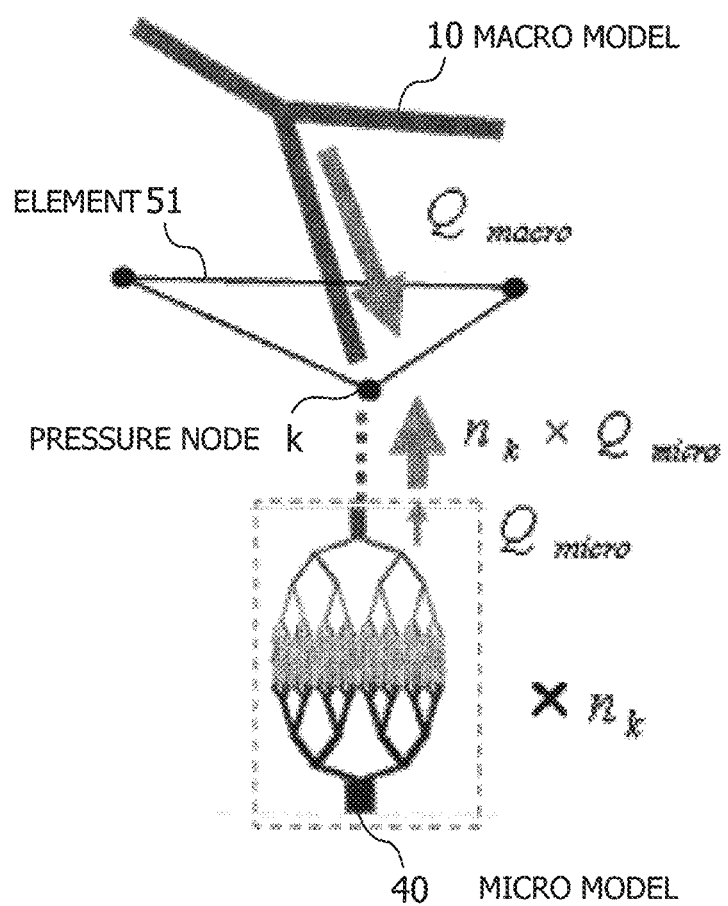
FIG. 6 illustrates how a macro model is connected to micro models via a pressure node.

FIG. 6 illustrates how a macro model is connected to micro models via a pressure node. The illustrated macro model 10 particularly represents a blood vessel network that belongs to the arterial system. The person skilled in the art would appreciate that FIG. 6 similarly applies to the venous side of this simulation model as well. Seen in the center of FIG. 6 is an element 51 of the finite element model, in the form of a polyhedron obtained by placing line segments to interconnect adjacent pressure nodes. This element 51 includes a pressure node k via which a plurality $n_k$ of micro models 40a are connected to the nearest vessel of the macro model 10.

On the arterial side, the blood flows from the macro model to a plurality $n_k$ of micro models 40 via a pressure node k. The macro model flow rate $Q_{macro}^{\gamma}$ is thus divided into $n_k$. On the venous side, the blood flows from $n_k$ micro models 40 into a vessel of the macro model via a pressure node. The micro model flow rates $Q_{micro}^{\gamma}$ of these $n_k$ flows are combined into one. The direction of a micro model blood flow is expressed in the sign of $Q_{micro}^{\gamma}$. Specifically, $Q_{micro}^{\gamma}$ takes a negative value when it represents a blood flow from a macro model 10 to micro models 40 as depicted in FIG. 6. Accordingly, the sum of the macro flow $Q_{macro}^{\gamma}$ and $n_k$ times the micro flow $Q_{micro}^{\gamma}$ is always zero as seen in equation (2).

(c) Computation Algorithms

This section describes computation algorithms used in the proposed coronary circulation simulation. For exemplary purposes, the following description assumes the use of a Newton-Raphson method for nonlinear analysis. According to the first embodiment, the problem is solved by using parallel computation based on the concept of multi-scale analysis. The entire system is given by the following matrix equation (3).

$$\begin{pmatrix} A_{Mic} & C^T \\ C & B_{Mac} \end{pmatrix} \begin{pmatrix} \Delta \mu_{Mic} \\ \Delta \mu_{Mac} \end{pmatrix} = \begin{pmatrix} r_{Mic} \\ r_{Mac} \end{pmatrix} \quad (3)$$

$A_{Mic}$ is a coefficient matrix produced from a micro model of vessels. $B_{Mac}$ is a coefficient matrix produced from a macro model of vessels. C is a matrix representing connections between the micro portion and the macro portion. $C^T$ denotes the transposed matrix of C. $\Delta \mu_{Mic}$ represents increments of micro-model pressure in the nonlinear analysis, while $\Delta \mu_{Mac}$ is the same for macro model pressure. Lastly, $r_{Mic}$ represents residuals produced in the nonlinear analysis of the micro model, while $r_{Mac}$ is the same for the macro model.

The coefficient matrix in equation (3) is broken into a product of two matrices as follows.

$$\begin{pmatrix} A_{Mic} & C^T \\ C & B_{Mac} \end{pmatrix} = \begin{pmatrix} A_{Mic} & 0 \\ C & \tilde{B}_{Mac} \end{pmatrix} \begin{pmatrix} I & A_{Mic}^{-1} C^T \\ 0 & I \end{pmatrix} \quad (4)$$

$$\tilde{B}_{Mac} = B_{Mac} - C A_{Mic}^{-1} C^T$$

Based on this equation (4), the following three steps yield pressure increments in the micro and macro models.

1. Calculate $\Delta\tilde{\mu}_{Mic}$ from $A_{Mic}\Delta\tilde{\mu}_{Mic}=r_{Mic}$ (5)

2. Calculate $\Delta\mu_{Mac}$ from $\tilde{B}_{mac}\Delta\mu_{Mac}=r_{Mac}-C\Delta\tilde{\mu}_{Mic}$ (6)

3. Calculate $\Delta\mu_{Mic}$ from $\Delta\mu_{Mic}=\Delta\tilde{\mu}_{Mic}-A_{Mic}^{-1}C^T\Delta\mu_{Mac}$. (7)

The first step seen in equation (5) converts the micro model equation into another form that eliminates the increments of macro-model pressure. This calculation yields tentative pressure increments $\Delta\mu_{Mic}$ in the micro models. (Note that there is a tilde on top of μ.) The second step seen in equation (6) then calculates pressure increments in the macro model by using the tentative pressure increments obtained from the micro models. The third step seen in equation (7) uses these pressure increments of the macro model to calculate true pressure increments that the micro models are supposed to have.

The above steps remove the degrees of freedom of micro models so as not to intrude the macro model matrix, thus making it possible to separate micro model calculation from macro model calculation. Here the micro models are perfectly independent of each other. For this reason, the parallel processors can process their assigned micro models without interactions, thus achieving efficient computation of coronary circulation.

(d) Use of Symmetry to Reduce Computational Load

As discussed previously, the first embodiment uses a symmetric model 30 for modeling medium-scale vessels in the intermediate layer that connects a macro model with capillaries. The use of such a symmetric model reduces the amount of computation. The following section demonstrates how the first embodiment takes advantage of the symmetry, by using the simplest example, i.e., a bifurcated vessel formed from three elements and four nodes.

Figure 7:
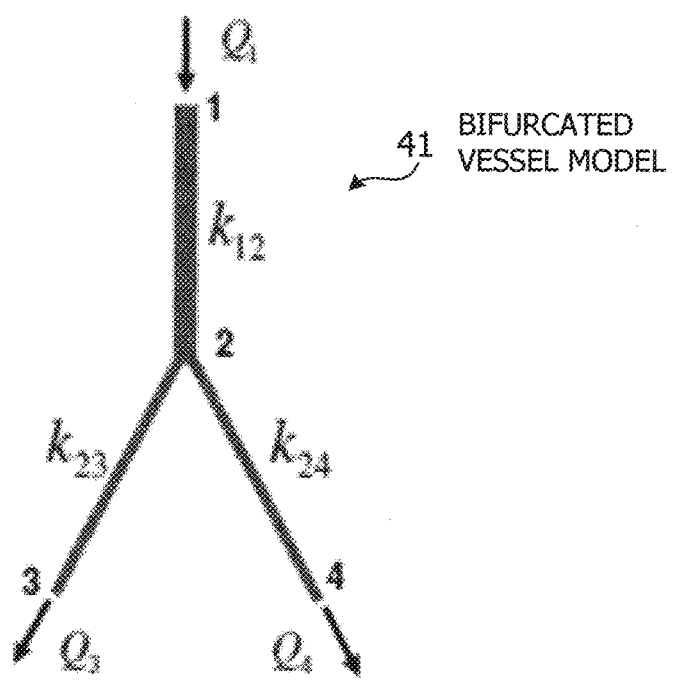
FIG. 7 depicts an example of a bifurcated vessel model.

FIG. 7 depicts an example of a bifurcated vessel model. The illustrated bifurcated vessel model 41 represents a part of the arterial system. Specifically, this bifurcated vessel model 41 divides one upper-scale vessel into two lower-scale vessels. The numerals placed beside each end of these vessels are node numbers. Suppose now that blood flows into the upper-scale vessel at a rate of $Q_1$ while blood flows out of the two lower-scale vessels at respective rates of $Q_2$ and $Q_3$.

The conductance of each vessel is defined as follows. Here the conductance indicates how easily the blood passes, and its inverse quantity is resistance. The higher the conductance of vessels is, the easier the blood can flow through them. The symbol $k_{ij}$ is used for the conductance of a vessel section between the ith node and the jth node, where i and j are integers greater than zero. For example, $k_{12}$ represents the conductance of a vessel between node #1 and node #2.

The blood flow in the illustrated bifurcated vessel is expressed below in equation (8), under the simplified condition that the flow is determined solely from the vessel conductance.

$$\sum_{j\in F_i} k_{ij}(t)(\mu_i - \mu_j) + \sum_{j\in F_i} \frac{dV_i(t)}{dt} = 0 \quad (8)$$

Based on this equation (8), a stiffness matrix is produced as follows.

$$\begin{bmatrix} k_{12} & -k_{12} & 0 & 0 \\ -k_{12} & k_{12}+k_{23}+k_{24} & -k_{23} & -k_{24} \\ 0 & -k_{23} & k_{23} & 0 \\ 0 & -k_{24} & 0 & k_{24} \end{bmatrix} \begin{Bmatrix} \mu_1 \\ \mu_2 \\ \mu_3 \\ \mu_4 \end{Bmatrix} = \begin{Bmatrix} Q_1 \\ 0 \\ Q_3 \\ Q_4 \end{Bmatrix} \quad (9)$$

In these equations (8) and (9), $Q_i$ is the flow rate of blood into node #i, $F_i$ represents a set of nodes that connect to node #i, $\mu_i$ denotes the blood pressure at node #i, and V is the volume of a vessel passage.

The two lower-scale vessels branching from the upper-scale vessel are supposed to be exactly symmetrical in terms of the diameter and length, as well as in the way of forming subsequent branches. This symmetry of vessels leads to:

$k_{23}=k_{24}$ $\mu_3=\mu_4$ $Q_3=Q_4$

The matrix equation is therefore reduced as follows.

$$\begin{bmatrix} k_{12} & -k_{12} & 0 \\ -k_{12} & k_{12}+2k_{23} & -2k_{23} \\ 0 & -2k_{23} & 2k_{23} \end{bmatrix} \begin{Bmatrix} \mu_1 \\ \mu_2 \\ \mu_3 \end{Bmatrix} = \begin{Bmatrix} Q_1 \\ 0 \\ 2Q_3 \end{Bmatrix} \quad (10)$$

With this reduction, equation (10) is solved with a smaller amount of computation.

As can be seen from the above explanation, the first embodiment implements a multi-scale analysis by taking advantage of anatomical features of the blood vessel network. That is, micro models 40 are defined on the basis of the feature that their microcirculatory systems are connected together only via larger vessels. These micro models 40 are connected to a macro model 10 at each node of the geometric model. The proposed method reduces the amount of data to be processed in the analysis because a microcirculation model 20 including capillaries can be analyzed with a unified structure of micro models 40. In addition, connections between macro models 10 and micro models 40 are allowed only at the pressure nodes. This restriction also contributes to a reduced processing load because of the fewer choices for locations provided from a plurality of second analyzing units 3*a*, 4*a*, 5*a*, . . . to the first analyzing unit 2*a*. Parallel processing techniques can be used to analyze micro models connected to many nodes because they are independent of each other.

The above-described first embodiment provides a computation algorithm suitable for parallel processing to reduce the simulation time. Unlike the conventional circulatory simulation, the first embodiment reproduces the structure of vessels down to the capillary level, besides making it possible to simulate the beating of cardiac muscle. The first embodiment also reduces the amount of computational operations and thus enhances the simulation speed, by taking advantage of the symmetry of medium-scale vessels extending between microcirculatory vessels and large vessels.

(B) Second Embodiment

This section describes a second embodiment which executes a coronary circulation simulation with a parallel computing system formed from a plurality of computing nodes each having one or more multi-core CPUs.

Figure 8:
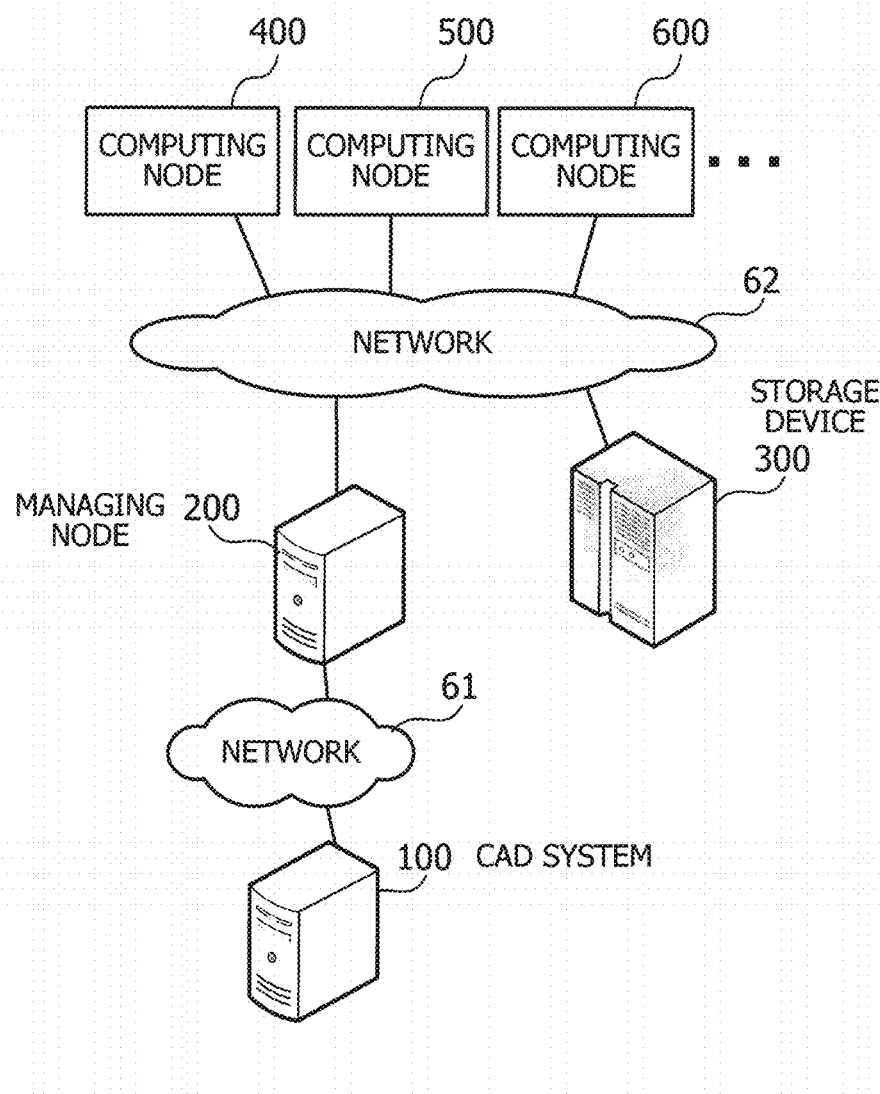
FIG. 8 illustrates an exemplary system configuration according to a second embodiment.

FIG. 8 illustrates an exemplary system configuration according to the second embodiment. The second embodiment includes a computer-aided design (CAD) system 100 for the purpose of modeling a three-dimensional heart structure and coronary vessel network, through the user interaction. The CAD system 100 is linked to a managing node 200 via a network 61. The CAD system 100 sends the created models of three-dimensional heart structure and coronary vessel network to the managing node 200, along with an execution command for a coronary circulation simulation based on those models.

The managing node 200, on the other hand, is connected to a storage device 300 and a plurality of computing nodes 400, 500, 600, . . . via another network 62. The managing node 200 uses the storage device 300 to store data of the above-noted models supplied from the CAD system 100. When an execution command requesting a coronary circulation simulation is received from the CAD system 100, the managing node 200 submits jobs to each computing node 400, 500, 600, . . . to initiate the requested simulation. This job submission processing includes, for example, sending various files and parameters from the managing node 200 to computing nodes, such as information about of storage locations of model data, and programs and parameters for use in the jobs.

The storage device 300 stores data of the models that the user has created with the CAD system 100. The storage device 300 includes a plurality of hard disk drives or solid state drives (SSD). These drives may be configured with the Redundant Array of Independent Disks (RAID) technology.

The computing nodes 400, 500, 600, . . . run in parallel to execute a coronary circulation simulation in accordance with commands from the managing node 200. Since multi-core CPUs are used in these computing nodes 400, 500, 600, . . . each individual node is capable of executing multiple processes concurrently.

Figure 9:
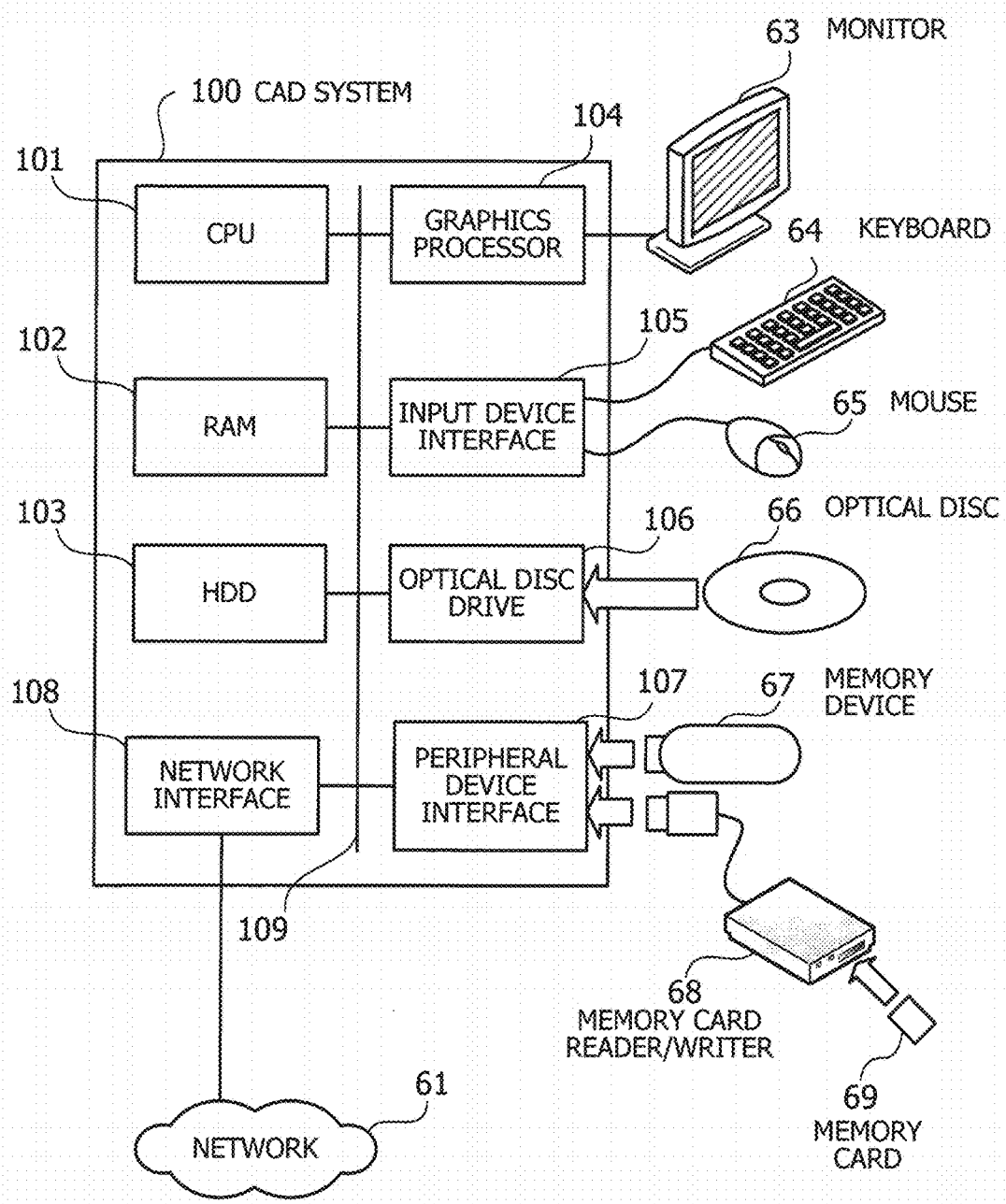
FIG. 9 depicts an exemplary hardware structure of a CAD system.

FIG. 9 depicts an exemplary hardware structure of a CAD system. The illustrated CAD system 100 includes a CPU 101 to control its entire operation. The CPU 101 is connected to a RAM 102 and other various devices and interfaces on a bus 109. While FIG. 9 illustrates a single CPU configuration, the CAD system 100 may have two or more such CPUs. When that is the case, the CPUs work in a coordinated way to control the entire system.

The RAM 102 serves as primary storage of the CAD system 100. Specifically, the RAM 102 is used to store at least some of the operating system (OS) programs and application programs that the CPU 101 executes, in addition to other various data objects that it manipulates at runtime.

Other devices on the bus 109 include an HDD 103, a graphics processor 104, an input device interface 105, an optical disc drive 106, a peripheral device interface 107, and a network interface 108. The HDD 103 writes and reads data magnetically on its internal platters. The HDD 103 serves as secondary storage of the CAD system 100 to store program and data files relating to the operating system and applications. Flash memory and other semiconductor memory devices may also be used as secondary storage, similarly to the HDD 103.

The graphics processor 104, coupled to a monitor 63, produces video images in accordance with drawing commands from the CPU 101 and displays them on a screen of the monitor 63. The monitor 63 may be, for example, a cathode ray tube (CRT) display or a liquid crystal display.

The input device interface 105 is used to connect input devices such as a keyboard 64 and a mouse 65 and supply signals from these devices to the CPU 101. The mouse 65 is a pointing device, which may be replaced with other kinds of pointing devices such as touchscreen, tablet, touchpad, and trackball.

The optical disc drive 106 reads out data encoded on an optical disc 66, by using laser light. The optical disc 66 is a portable data storage medium, the data recorded on which can be read as a reflection of light or the lack of the same. The optical disc 66 may be a digital versatile disc (DVD), DVD-RAM, compact disc read-only memory (CD-ROM), CD-Recordable (CD-R), or CD-Rewritable (CD-RW), for example.

The peripheral device interface 107 is a communication interface to attach peripheral devices to the CAD system 100. For example, the peripheral device interface 107 may be used to connect a memory device 67 and a memory card reader/writer 68. The memory device 67 is a data storage medium with a capability to communicate with the peripheral device interface 107. The memory card reader/writer 68 is an adapter used to write data to or read data from a memory card 69, which is a data storage medium in the form of a small card. The network interface 108 is connected to a network 61 to exchange data with other computers or network devices (not illustrated).

Figure 10:
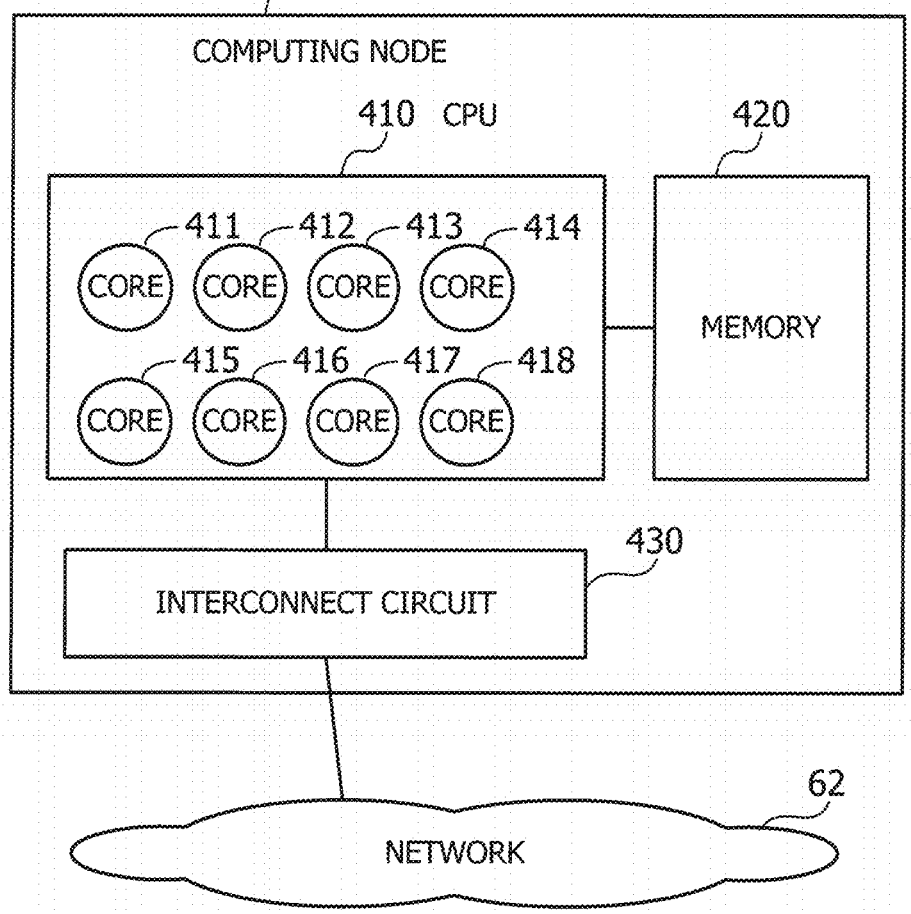
FIG. 10 depicts an exemplary hardware configuration of a computing node.

FIG. 10 depicts an exemplary hardware configuration of a computing node. The illustrated computing node 400 includes a CPU 410, a memory 420, and an interconnect circuit 430. The CPU 410 is a multi-core processor containing a plurality of processor cores 411 to 418 capable of executing multiple processes in parallel. The memory 420 stores programs that the CPU 410 executes, as well as various data that the CPU 410 needs to execute processing. For example, the memory 420 serves as a primary storage device to store programs for coronary circulation simulation. The interconnect circuit 430 is a communication circuit designed for high-speed optical communication. The interconnect circuit 430 is used to exchange data with other computing nodes 400, 500, 600, . . . via a network 62. The CPU 410 uses this interconnect circuit 430 to read data of a cardiac model from the storage device 300 via the network 62.

The above hardware configuration serves as a platform of processing functions to implement the second embodiment. That is, the CAD system 100, managing node 200, and computing nodes 400, 500, 600, . . . realize processing functions of the second embodiment by executing software programs, which may be stored in various computer-readable storage media. For example, these programs may be provided in HDDs. In each of the CAD system 100, managing node 200, and computing nodes 400, 500, 600, . . . , the CPU loads its local RAM with at least part of the programs stored in the HDD and executes them on the RAM. The programs files may be stored in portable storage media such as optical discs 66, memory devices 67, and memory cards 69. It is noted that the computer-readable storage media for those programs do not include transitory propagating signals.

Portable storage media, such as optical discs 66, memory devices 67, and memory cards 69, are used to distribute program products for sale. As another form of product distribution, the program files may be stored in a computer storage device, so that the CAD system 100, managing node 200, or computing nodes 400, 500, 600, . . . can download them from a server computer via the network 61. In this case, the CAD system 100, managing node 200, or computing nodes 400, 500, 600, . . . store the downloaded programs in their local RAM or HDD.

While the above description of FIGS. 8 to 10 has been directed to the second embodiment, the same hardware configurations may similarly apply to the foregoing simulator apparatus X of the first embodiment.

Figure 11:
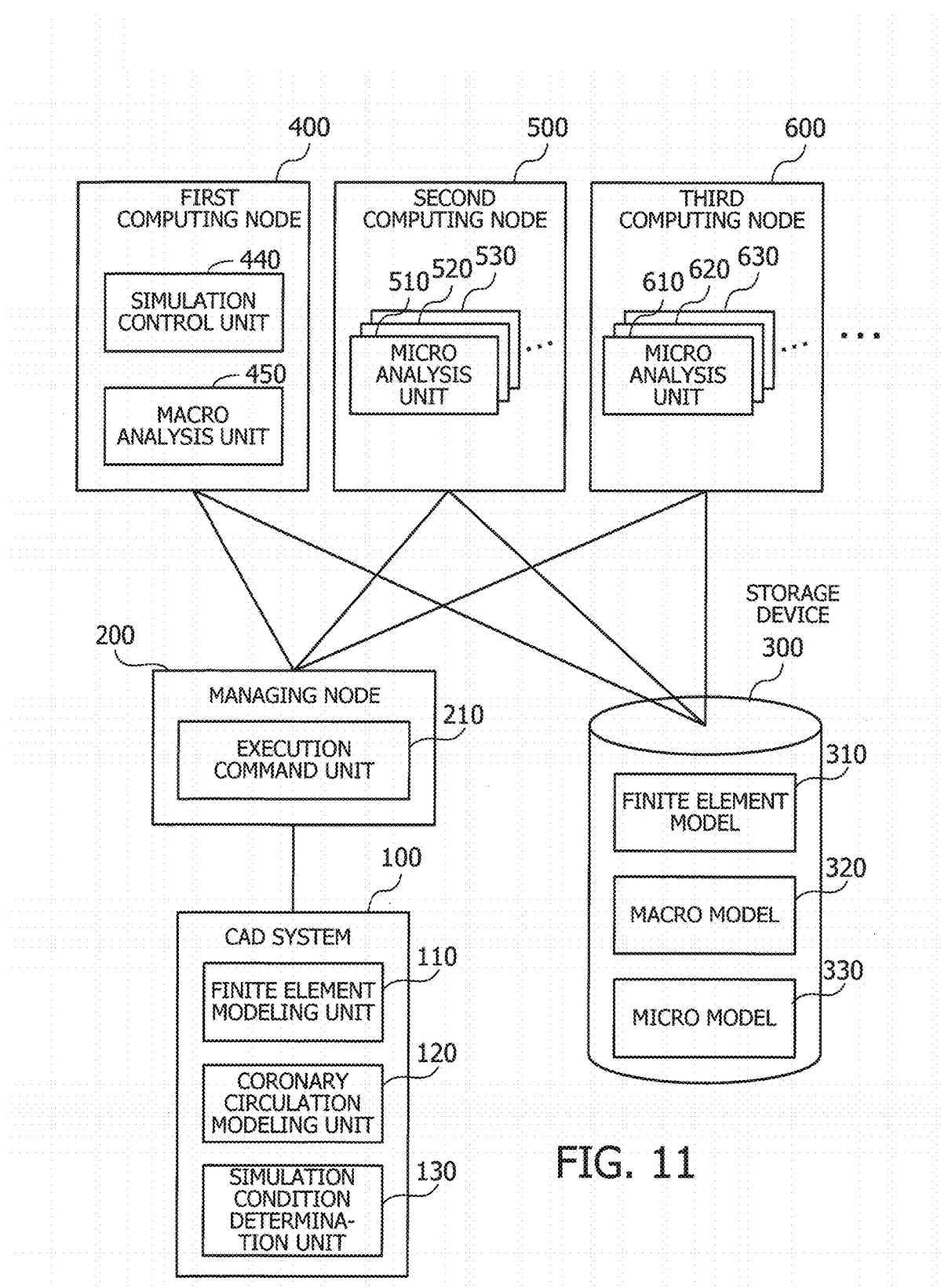
FIG. 11 is a functional block diagram of devices according to the second embodiment.

According to the second embodiment, the constituent components of the system provide their own functions as will be described below. FIG. 11 is a functional block diagram of components that constitute the second embodiment. The illustrated CAD system 100 includes a finite element modeling unit 110, a coronary circulation modeling unit 120, and a simulation condition determination unit 130. The finite element modeling unit 110 produces a finite element model representing the solid geometry of a heart, according to commands from the user. This finite element model may be organized as a three-dimensional mesh of, for example, tetrahedrons. The tetrahedral mesh has been mentioned in the first embodiment as an example of polyhedron elements.

According to commands from the user, the coronary circulation modeling unit 120 produces a coronary circulation model representing a blood vessel network of a heart. Also according to commands from the user, the simulation condition determination unit 130 determines under what conditions the coronary circulation simulation is to be executed. For example, the simulation condition determination unit 130 determines how many micro models to connect to each pressure node of the cardiac muscle.

The managing node 200 includes an execution command unit 210 configured to command a plurality of computing nodes 400, 500, 600, . . . to execute a coronary circulation simulation with the finite element model and coronary circulation model produced by using the CAD system 100. For example, the execution command unit 210 receives these two models from the CAD system 100 and stores them in a storage device 300. The execution command unit 210 then selects computing nodes to submit jobs of the coronary circulation simulation. For example, the execution command unit 210 may select every computing node that has no jobs to execute at the moment. In the case where a specific degree of parallelism is designated previously for the coronary circulation simulation, the execution command unit 210 selects as many computing nodes as needed to achieve the designated parallelism. The selected computing nodes are supposed to receive a job assignment. The execution command unit 210 further singles out one computing node for macro analysis while assigning the remaining computing nodes for micro analysis. The execution command unit 210 submits a job to the former computing node (e.g., the first computing node 400 in FIG. 11) to perform a macro analysis, as well as to control the entire process of simulation. The execution command unit 210 also submits jobs to the remaining computing nodes (e.g., the second, third, and subsequent computing nodes 500, 600, . . . in FIG. 11) to perform a micro analysis.

The storage device 300 stores a finite element model 310, a macro model 320, and a micro model 330. The finite element model 310 is an example of the geometric model 1a discussed in the first embodiment of FIG. 1. The macro model 320 is an example of the first vessel network model 1b discussed in the same. The micro model 330 is an example of the second vessel network model 1c discussed in the same. A coronary circulation model is formed by combining the macro model 320 and micro model 330.

The first computing node 400 includes a simulation control unit 440 and a macro analysis unit 450. The simulation control unit 440 controls the entire process of a coronary circulation simulation. The macro analysis unit 450 undertakes a macro-modeling part of the coronary circulation simulation, such as the analysis of heart beats produced by myocardial contraction and relaxation and the blood flows in large coronary arteries and veins. The simulation control unit 440 and macro analysis unit 450 are functions realized as part of macro analysis jobs submitted to the first computing node 400. The macro analysis unit 450 is an example of the first analyzing unit 2a discussed previously in the first embodiment of FIG. 1.

The second computing node 500 includes a plurality of micro-analysis units 510, 520, 530, . . . to analyze the blood flow in medium-scale vessels, arterioles venules, and capillaries. These micro analysis units 510, 520, 530, . . . are functions that are realized by a plurality of processor cores in the CPU which execute micro analysis jobs submitted to the second computing node 500.

The third computing node 600 similarly includes a plurality of micro analysis units 610, 620, 630, . . . to analyze the blood flow in medium-scale vessels, arterioles venules, and capillaries. These micro analysis units 610, 620, 630, . . . are functions that are realized by a plurality of processor cores in the CPU which execute micro analysis jobs submitted to the second computing node 600.

The above micro analyzing units in the computing nodes 500, 600, . . . are an example of the second analyzing units 3a, 4a, 5a, . . . discussed in the first embodiment of FIG. 1. The lines interconnecting the functional blocks in FIG. 11 are only an example. FIG. 11 omits some communication paths for simplicity purposes. The person skilled in the art would appreciate that there may be other communication paths in the actual implementations.

Simulation models stored in the storage device 300 will now be described in greater detail below. FIG. 12 illustrates an exemplary data structure of a finite element model. This finite element model 310 includes a node data table 311 and a mesh data table 312, in which $N_{nodes}$ and $N_{mesh}$ respectively denote the total number of nodes and the total number of meshes.

The node data table 311 is a collection of coordinates that indicate the position of each node constituting tetrahedral meshes. Each table entry includes the node number identifying a node and the x, y, and z-axis coordinate values indicating the node's position in a three-dimensional virtual space.

The mesh data table 312 is a set of data that defines the geometry of meshes. Each table entry represents a specific tetrahedral mesh identified by its mesh number and defines its shape as a set of node numbers indicating which nodes constitute the tetrahedron.

FIG. 13 illustrates an exemplary data structure of a macro model. This macro model 320 represents a structure of large coronary arteries and veins as part of the cardiac vessel network. Included in the macro model 320 are a node data table 321 and a vessel element data table 322. The node data table 321 is similar to the node data table 311 in the finite element model 310 of FIG. 12. $N_{elem}$ represents the total number of vessel elements.

The vessel element data table 322 is formed from the following data fields: element number, node, level, radius, and conductance. The element number field contains a number for identifying each specific vessel element. The node field contains the identifiers of two nodes at the opposite ends of a vessel element. The level field indicates the "level" of a vessel element. Greater level values are given to larger vessels. It is capillaries that are classified as the smallest level. The radius field indicates the radius of a vessel, and the conductance field contains a value indicative of how easily the blood flows through the vessel. A higher conductance means that the blood flows more smoothly with a smaller resistance.

FIG. 14 illustrates an exemplary data structure of a micro model. This micro model 330 represents a structure of intermediate vessel network, arterioles, venules, and capillaries as part of the cardiac vessel network. Included in the micro model 330 are a node data table 331 and a vessel element data table 332. The node data table 331 is similar to the node data table 311 in the finite element model 310 of FIG. 12. $N_{elem}$ represents the total number of vessel elements.

The vessel element data table 332 is formed from the following data fields: element number, node, level, length, diameter, vessel wall elasticity, reference pressure difference, and quantity. The element number field contains a number for identifying each specific vessel element. The node field contains the identifiers of two nodes at the opposite ends of a vessel element. The level field indicates the above-described level of a vessel element. The length and diameter fields respectively indicate the length and diameter of a vessel element. The vessel wall elasticity fields contains an elasticity coefficient of walls of a vessel element. The reference pressure difference field gives a reference value of pressure difference between the blood pressure within a vessel and the inner pressure of the myocardium. This reference value is used together with a pressure difference at each simulation time point to calculate the diameter of the vessel. The quantity field indicates how many elements are present in the same level, under the assumption of symmetry.

The foregoing functional blocks of FIG. 11 work in a coordinated way to execute a coronary circulation simulation, using the data seen in FIGS. 12 to 14.

Figure 15:
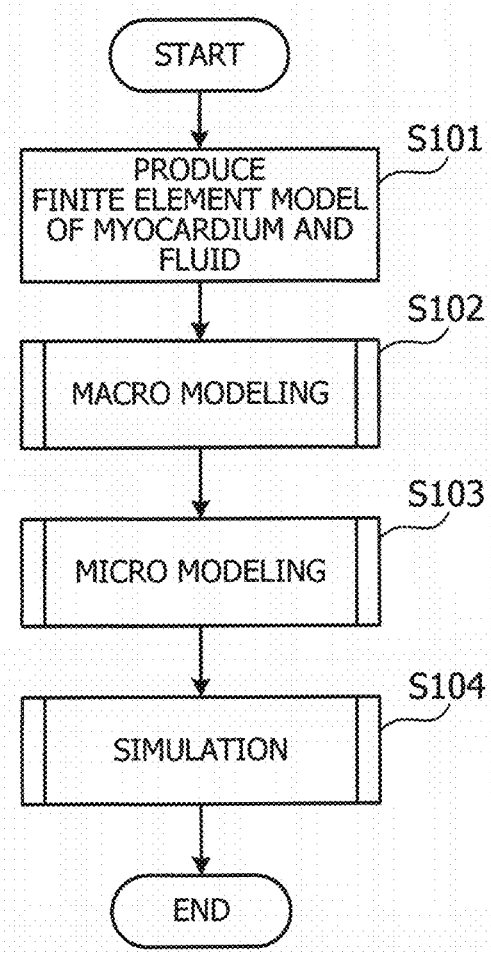
FIG. 15 is a flowchart illustrating an exemplary procedure of a coronary circulation simulation.

FIG. 15 is a flowchart illustrating an exemplary procedure of a coronary circulation simulation. Each operation in FIG. 15 is described below in the order of step numbers.

(Step S101) The user interacts with the CAD system 100 to initiate a simulation. The finite element modeling unit 110 in the CAD system 100 produces a finite element model 310 according to the user input. The produced finite element model 310 is sent to the managing node 200, and the managing node 200 stores it in the storage device 300.

(Step S102) The coronary circulation modeling unit 120 in the CAD system 100 produces a macro model 320 according to the user input. The produced macro model 320 is sent to the managing node 200, and the managing node 200 stores it in the storage device 300.

(Step S103) The coronary circulation modeling unit 120 produces a micro model 330 according to the user input. The produced micro model 330 is sent to the managing node 200, and the managing node 200 stores it in the storage device 300.

(Step S104) The execution command unit 210 in the managing node 200 submits jobs to a plurality of computing nodes and requests them to execute a coronary circulation simulation. The computing nodes execute the simulation as requested, by using a plurality of processor cores in parallel.

Each of the above steps of FIG. 15 will now be described in detail below.

i) Finite Element Modeling

The CAD system 100 receives medical image data of, for example, the Computed Tomography (CT) or the Magnetic Resonance Image (MRI), Echocardiogram. The finite element modeling unit 110 extracts geometric data of the heart from the received image and divides the data into meshes (e.g., tetrahedral or hexahedral meshes) suitable for the finite element method.

ii) Coronary Circulation Network Modeling

The modeling process of a coronary circulation network is divided to two parts, macro modeling and micro modeling. More specifically, vessels may be mimicked in either a macro model or a micro model depending on their dimensions. For example, Kassab measured and classified the vessel diameters into several levels (see, for example, the first to third non-patent documents listed in a previous section). The data of these diameter levels may be used to assign the vessels to macro and micro models as follows:

Macro model to include arteries of level 6 to level 11 and veins of level −6 to level −12.

Micro model to include medium-scale arteries of level 3 to level 5, medium-scale veins of level −3 to level −5, and microcirculatory vessels of level 3 and below, as well as of level −3 and above.

Figure 16:
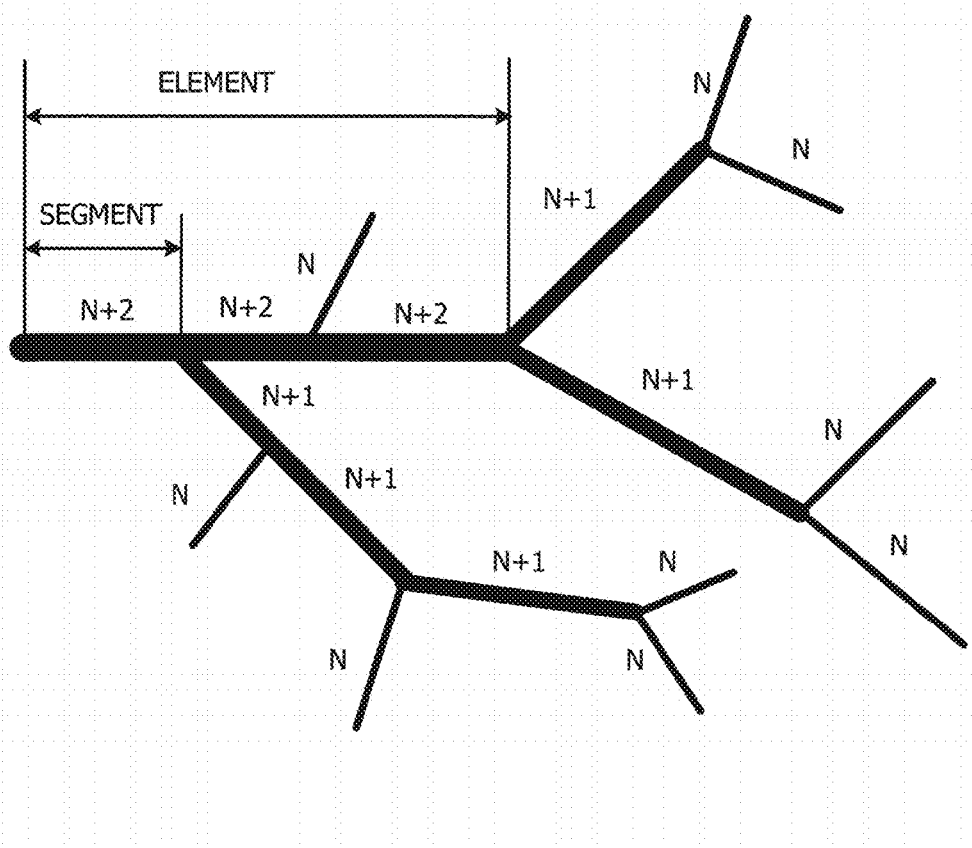
FIG. 16 illustrates exemplary classification of vessels in a coronary circulation model.

Such diameter levels of vessels will be discussed in greater detail below. FIG. 16 illustrates exemplary classification of vessels in a coronary circulation model. As seen, one large vessel branches out into small vessels. The coronary circulation modeling unit 120 refers to each section between the nearest branching points as a "segment." The coronary circulation modeling unit 120 sorts those segments into several levels based on the diameters of the segments. It is also noted that in the example of FIG. 16, a series of segments of identical levels is referred to as an "element."

The coronary circulation modeling unit 120 starts with a capillary and traces the branches toward a larger vessel, while assigning an appropriate level to each segment on the way. For example, the coronary circulation modeling unit 120 classifies segments with diameters of 8 μm or less as capillaries and assigns level 0 to them. The coronary circulation modeling unit 120 then proceeds from the capillaries toward the trunk of the tree structure. Suppose, for example, that two vessels of level N combine together into an upper-scale vessel. The coronary circulation modeling unit 120 detects this and assigns level N+1 to the upper-scale vessel, where N is a positive integer or zero. In the case where two vessels of different levels meet at a point, the coronary circulation modeling unit 120 determines which segment has a higher level and assigns that higher level to the resulting upper-scale segment. Suppose, for example, that a segment of level N combines with a segment of level N+1. In this case, the subsequent upper-scale segment is qualified to be level N+1. The coronary circulation modeling unit 120 basically follows the above rules when selecting levels, with some modifications depending on the diameters of segments.

Based on the above measurement, the coronary circulation modeling unit 120 further calculates a mean and a standard deviation of the following quantities for each different level of vessels:

vessel diameter vessel length segment-to-element ratio (SN)

connectivity matrix (ER)

SN means how many segments are successively connected without changing their vessel levels.

Connectivity matrix is expressed as ER(M, N), where M is a positive integer or zero. ER(M, N) represents the occurrences of branching of level N vessels from the nodes on a level M vessel. While capillaries are classified as level 0 by definition, the coronary circulation modeling unit 120 further subdivides them into four classes C0a, C00, C0v, and Ccc. C0a means capillaries connected to the extreme end of arteries. C0v means capillaries connected to the extreme end of veins. C00 means capillaries running in parallel with the myocardium. Ccc means capillaries running perpendicularly to the longitudinal direction of the myocardium.

iii) Macro Modeling

Upon completion of the vessel classification described above, the coronary circulation modeling unit 120 produces a macro model from arteries of level 6 to level 11 and veins of level −6 to level −12.

Figure 17:
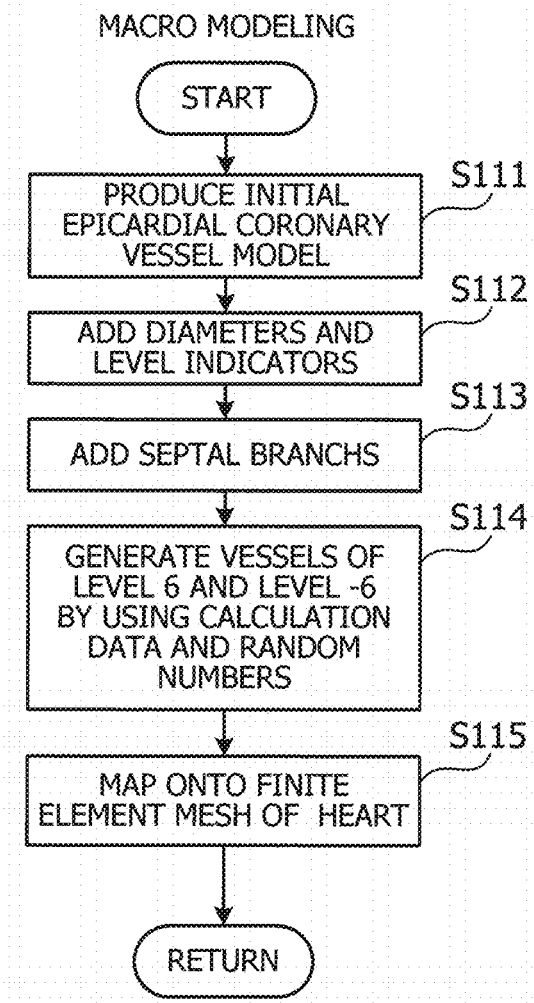
FIG. 17 is a flowchart illustrating an example of a macro modeling process.

FIG. 17 is a flowchart illustrating an example of a macro modeling process. Each operation in FIG. 17 is described below in the order of step numbers.

(Step S111) The coronary circulation modeling unit 120 produces an initial epicardial coronary vessel model. For example, the coronary circulation modeling unit 120 first produces an initial version of epicardial coronary vessel data from given tomographic images of the heart. The coronary circulation modeling unit 120 then maps this epicardial coronary vessel data on the outer wall of left and right ventricles in the cardiac finite-element model, thereby producing an initial epicardial coronary vessel model.

(Step S112) The coronary circulation modeling unit 120 puts some additional data to the initial epicardial coronary vessel model, which includes vessel diameters, levels, and presence of branches at each node. Here the network model 12 may be configured to display the produced epicardial coronary vessel model on a monitor screen.

Figure 18:
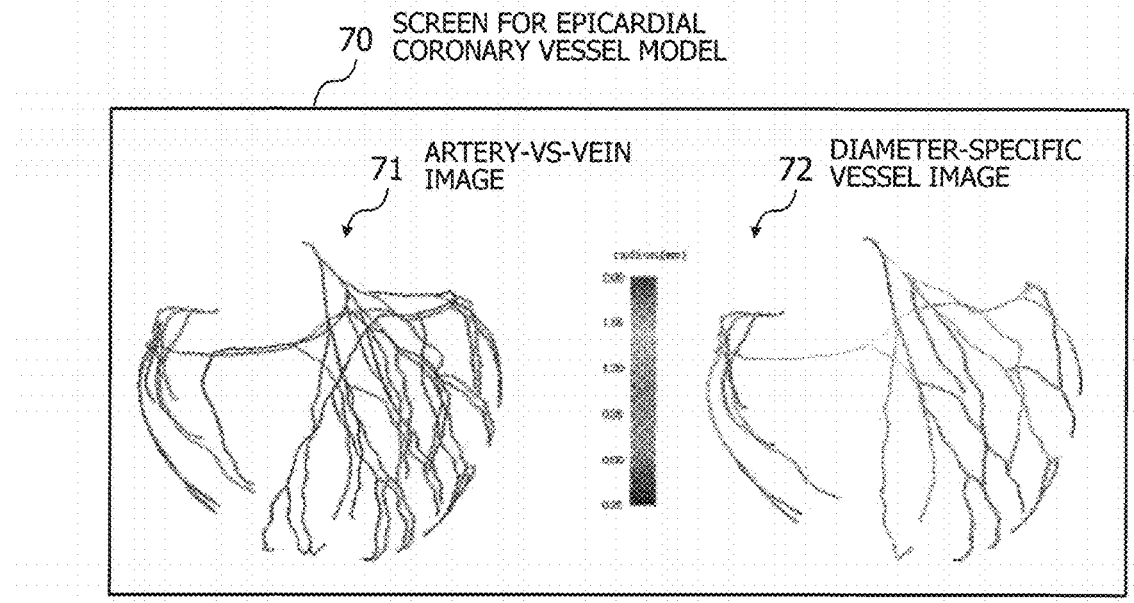
FIG. 18 illustrates an exemplary view of an epicardial coronary vessel model.

FIG. 18 illustrates an exemplary view of an epicardial coronary vessel model. In this example, the illustrated screen 70 for an epicardial coronary vessel model includes an artery-vs-vein image 71 on the left and a diameter-specific vessel image 72 on the right. The artery-vs-vein image 71 visualizes arteries and veins by using different colors. The diameter-specific vessel image 72 visualizes vessel diameters by using color gradations.

(Step S113) Referring back to FIG. 17, the coronary circulation modeling unit 120 adds septal branches to the epicardial coronary vessel model. Septal branch is the name of some particular vessels of the heart, which can be seen in microscope photographs and the like.

Figure 19:
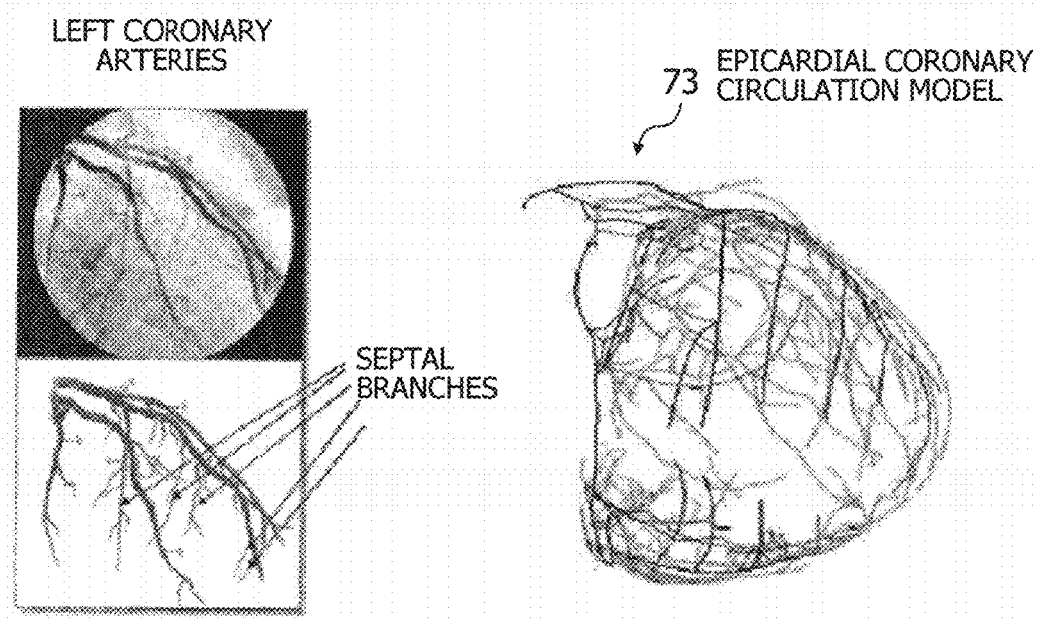
FIG. 19 illustrates an example of an epicardial coronary circulation model with septal branches.

FIG. 19 illustrates an example of an epicardial coronary circulation model with septal branches. As in the example of FIG. 19, the ramification of septal branches from arteries and veins may be seen in microscope photographs or anatomical charts. Based on such charts, the coronary circulation modeling unit 120 produces an epicardial coronary circulation model 73 having septal branches.

(Step S114) Referring back to FIG. 17, the coronary circulation modeling unit 120 produces blood vessel networks of level 6 or above, as well as those of level −6 or below, by using some calculation data and random numbers.

More specifically, the coronary circulation modeling unit 120 first determines the level of vessels branching out from nodes of the initial epicardial coronary vessels. Think of, for example, a lower-scale vessel branches out from a vessel of level N. The coronary circulation modeling unit 120 determines the level of this lower-scale vessel by using the connectivity matrix ER(N, x) and a random number between zero and one. In the case where the original vessel bifurcates at its end, the coronary circulation modeling unit 120 determines the level of these two lower-scale vessels. The coronary circulation modeling unit 120 then generates a random number, assuming that the segment-to-element ratio SN of each level is normally distributed with the mean and standard deviation calculated from the measurement values. The coronary circulation modeling unit 120 now determines the number of segments constituting the lower-scale vessel(s) by rounding off the generated random number to the nearest integer.

Similarly to SN, the coronary circulation modeling unit 120 assumes that the vessel diameter and length are also normally distributed with their respective mean values and standard deviations calculated from the measurement values. The coronary circulation modeling unit 120 determines the vessel diameter by using a random number generated according to the assumed normal distribution. This diameter is applied throughout the vessel element in question. The length of each vessel segment is also determined from a random number generated on the basis of its own statistical distribution. In this way, the coronary circulation modeling unit 120 produces blood vessel networks.

(Step S115) Lastly, the coronary circulation modeling unit 120 maps the produced blood vessel network to finite-element meshes of the heart model, thus producing a macro model 10 as discussed previously in FIG. 2.

iv) Micro Modeling

Figure 20:
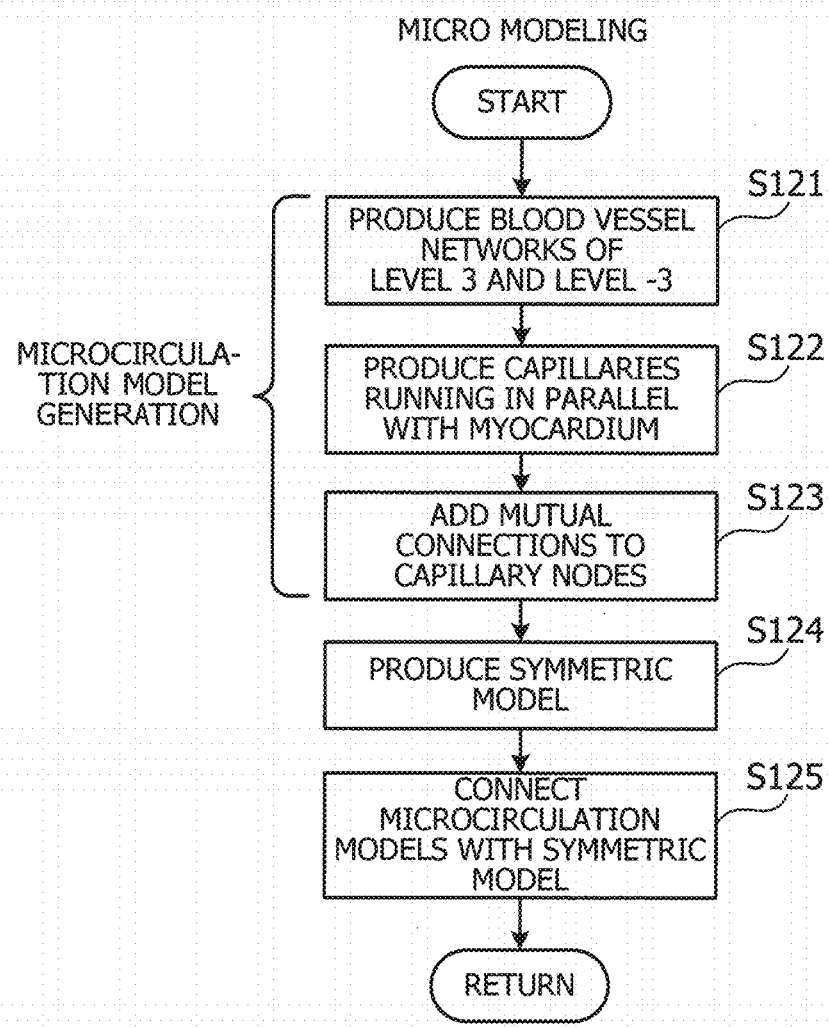
FIG. 20 is a flowchart illustrating an example of a micro modeling process.

The coronary circulation modeling unit 120 proceeds to micro model generation. FIG. 20 is a flowchart illustrating an example of a micro modeling process. Each operation in FIG. 20 is described below in the order of step numbers.

The coronary circulation modeling unit 120 begins the process with producing a microcirculation model at steps S121 to S123. This microcirculation model represents arterioles of level 3 to level 1, capillaries (vessels of level 0), and venules of level −3 to level −1 in a combined way. The microcirculation model is distinct in its network structure, which is unlike the foregoing macro model having a tree structure of bifurcated branches to represent large coronary vessels. For example, the microcirculatory system may be formed between one arteriole and two venules, with a longitudinal size of about 500 μm. To reproduce such vessels in a model, the coronary circulation modeling unit 120 introduces some additional constraints into the algorithm of generating a tree of vessel branches. More specifically, the coronary circulation modeling unit 120 produces a network of the microcirculation model under the following three conditions:

Condition 1: Capillaries originated from one arteriole (level 3) join together into two venules (level −3).

Condition 2: Capillaries are about 500 μl in longitudinal size.

Condition 3: Some nodes on the capillaries may be connected directly to each other.

The coronary circulation modeling unit 120 produces a microcirculation model by using measurement data and random numbers just as in the foregoing macro modeling method. More specifically, the following three steps S121 to S123 are executed to produce a microcirculation model.

(Step S121) The coronary circulation modeling unit 120 produces a network of level 3 arterial vessels and a network of level −3 venous vessels. For example, the coronary circulation modeling unit 120 produces an arterial branch model in a tree structure, based on the measurement data of Kassab et al. This model includes arterial vessels beginning with a level 3 arteriole and ending with level 1 arterioles. Similarly, the coronary circulation modeling unit 120 produces a venous branch model in a tree structure, beginning with two level −3 venules and ending with level −1 venules.

(Step S122) The coronary circulation modeling unit 120 produces capillaries running in parallel with the myocardium. For example, the coronary circulation modeling unit 120 extends the arterial vessels from their extreme ends by repetitively connecting capillary elements until the distance between the arterial end and the venous end is reduced to about 500 μm. Here the diameter and length of each capillary element are determined by modifying Kassab's measurement data with some random numbers. Because the number of arteries is not equal, in general, to that of their counterpart veins, the coronary circulation modeling unit 120 places additional branches at some capillary nodes to adjust this discrepancy in number, so that the two groups of vessels can be linked without any open ends. This modeling of capillary-level branches is in line with the actual observation of vessels. The coronary circulation modeling unit 120 determines the number of those branches according to the above-noted discrepancy in number between arteries and veins, besides stochastically selecting capillary nodes for the branching.

(Step S123) The coronary circulation modeling unit 120 adds some mutual connections to the capillary nodes. For example, the coronary circulation modeling unit 120 connects myocardial nodes with each other by placing additional vessel elements nearly perpendicular to the longitudinal direction of myocardial cells. Here the coronary circulation modeling unit 120 uses random numbers to determine the diameter and length of vessel elements as in the foregoing case of capillaries running in parallel with myocardial cells, besides stochastically selecting capillary nodes for the mutual connections.

Figure 21:
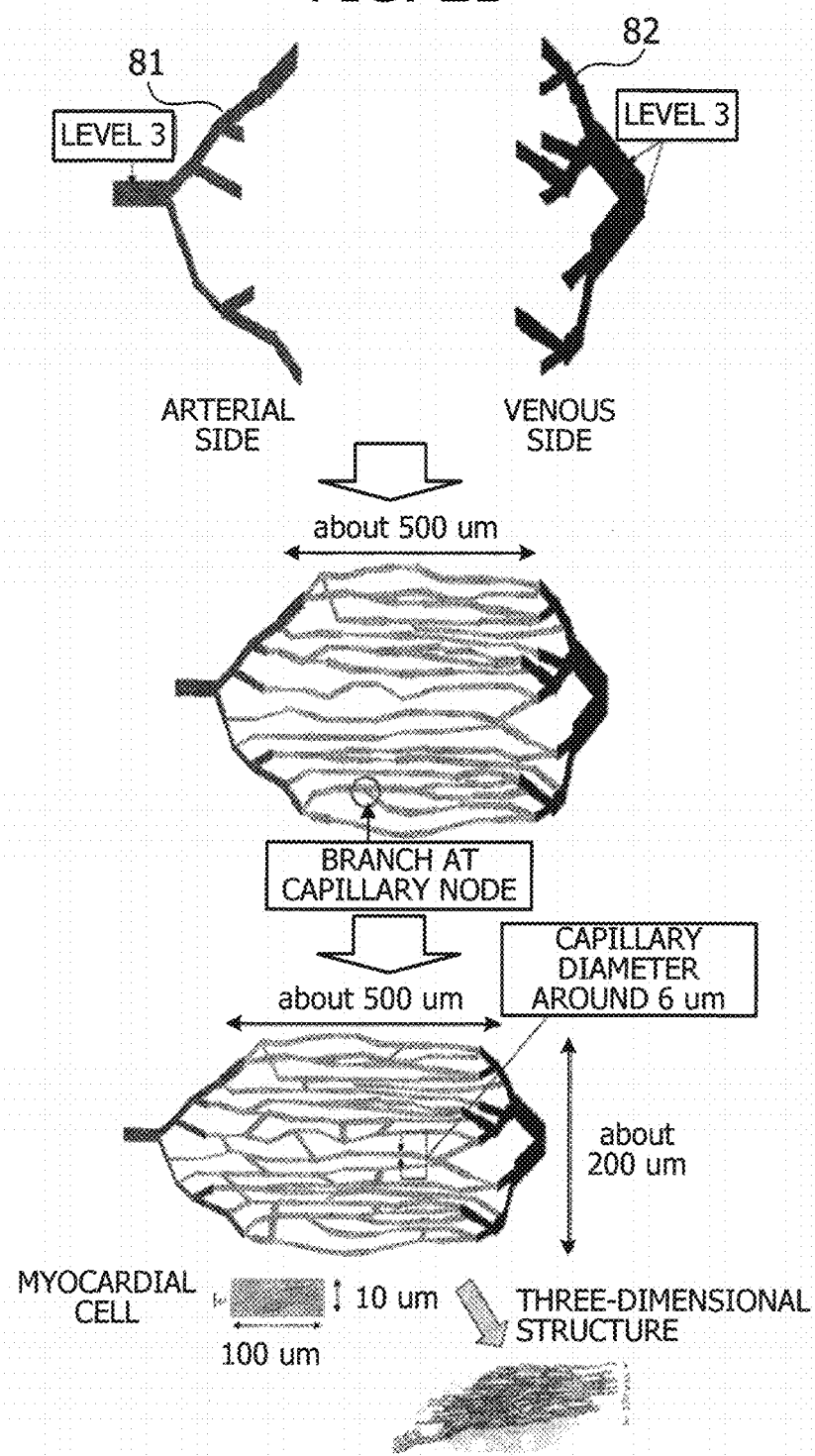
FIG. 21 depicts an exemplary procedure of building a microcirculation model.

The above three steps have produced a microcirculation model. FIG. 21 gives a specific example illustrating how these steps build a microcirculation model. At the outset, an arterial vessel network 81 of level 3 is produced at step S121, together with a venous vessel network 82 of level −3. Then capillaries with a size of about 500 μm are produced at step S122 to interconnect the arterial and venous vessel networks 81 and 82. These capillaries run in parallel with the myocardium and branch out at capillary nodes. At step S123, additional vessel elements are placed between some myocardial nodes, near perpendicular to the longitudinal direction of the myocardial cells. As depicted in FIG. 21, myocardial cells have a long and narrow shape, about 100 μm in the axial direction (longitudinal direction) and about 10 μm in the radial direction. The capillaries are, on the other hand, around 6 μm in diameter.

The microcirculation model built up in this way has a three-dimensional structure. Referring back to FIG. 20, S124 and subsequent steps will be explained below.

(Step S124) The coronary circulation modeling unit 120 produces a symmetric model. For example, this symmetric model extends from each end of the macro model until the microcirculation model is reached, while bifurcating seven times in that course. More specifically, the arteries branch out in the following way: level 5 (single vessel)-->level 5 (two vessels)-->level 5 (four vessels)-->level 4 (eight vessels)-->level 4 (16 vessels)-->level 4 (32 vessels)-->level 3 (64 vessels)-->level 3 (128 vessels)-->level 3 (reaching the top end of a microcirculation model). This similarly applies to the venous side of the symmetric model by adding a minus sign to the levels.

(Step S125) The coronary circulation modeling unit 120 connects microcirculation models with the symmetric model produced at step S124. The above symmetric model has 128 end points on each of the arterial and venous sides. The coronary circulation modeling unit 120 thus places 128 microcirculation models in parallel such that they are connected to each end of the macro model via the symmetric model.

As described above, the symmetric model includes three consecutive vessel elements of the same level. That is, there are three level 5 arteries, three level 4 arteries, and three level 3 arteries in the above example. The coronary circulation modeling unit 120 thus makes some fine modifications to the vessel diameters by using, for example, the mean value and standard deviation of each level of vessel elements. Specifically, the initial diameter of each three consecutive vessels is set to the mean value of a particular level of vessels. The modified diameters vary from (mean +σ) to (mean), and then to (mean −σ), where σ denotes the given standard deviation of these vessels. For the length of vessel elements, on the other hand, the coronary circulation modeling unit 120 uses the mean length of each relevant level.

Figure 22:
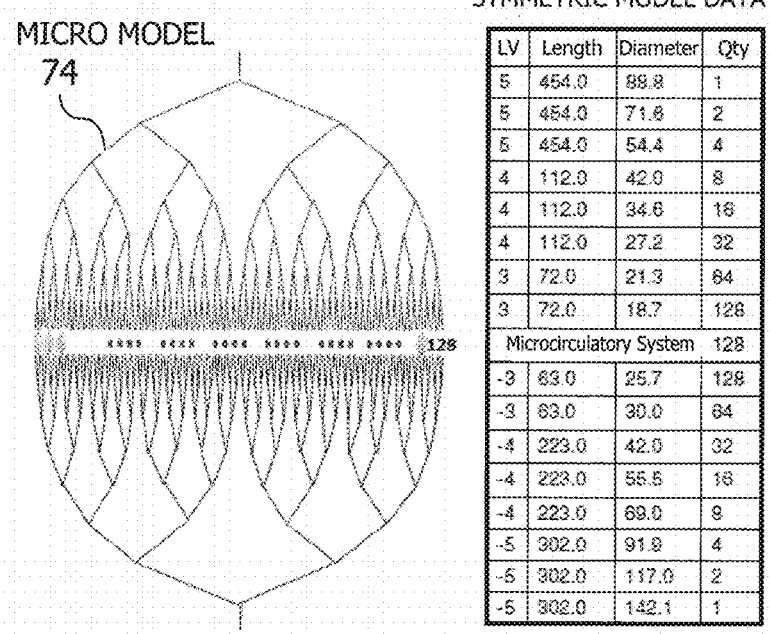
FIG. 22 illustrates an exemplary micro model in which 128 microcirculation models are connected in parallel at end points of a symmetrical model.

FIG. 22 illustrates an exemplary micro model in which 128 microcirculation models are connected in parallel at end points of a symmetrical model. As can be seen from FIG. 22, this micro model 74 includes a symmetric model in which the vessels bifurcate seven times in both the arterial and venous systems. Connected at the resulting end points of the symmetric model are 128 microcirculation models. The table in the right half of FIG. 22 gives the vessel levels, lengths, diameters, and quantities of peer vessels, where the lengths and diameters are in units of μm.

The above sections have described how the coronary circulation network model is produced. The following sections describe how the proposed method executes a simulation. More specifically, the description gives a detailed way of executing a coronary circulation simulation, beginning with how the number of micro models is determined for each pressure node of the myocardium. The description then proceeds to how the myocardium is coordinated with the microcirculation and explains computation algorithms for a multi-scale analysis.

(a) Determination of Micro Model Quantity

The density of small blood vessels per unit myocardial volume may vary with their depth in the cardiac walls. Taking this transmurality of vessel density into consideration, the simulation condition determination unit 130 assigns different relative vessel densities to the myocardial nodes depending on their depths. More specifically, a relative vessel density of 2.2 is assigned to myocardial nodes close to the endocardium (inner surface of myocardium) while a relative vessel density of 1 is assigned to myocardial nodes close to the epicardium (outer surface of myocardium).

Figure 23:
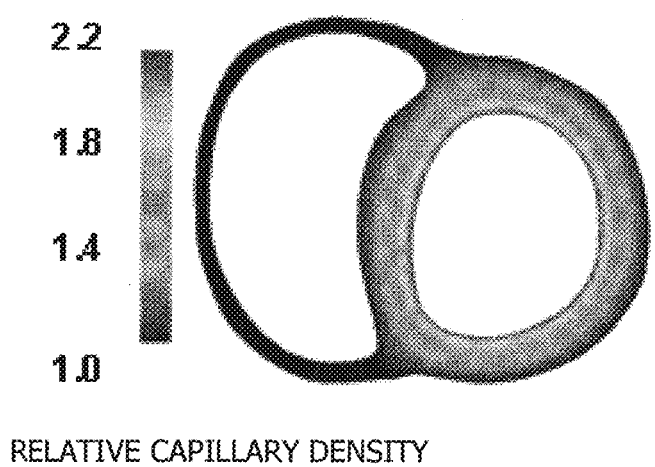
FIG. 23 illustrates a distribution of relative vessel density.

FIG. 23 illustrates the resulting distribution of relative vessel density. Specifically, FIG. 23 depicts a cross-section of the heart, with color gradation to represent relative vessel densities. Based on such relative vessel densities, the simulation condition determination unit 130 determines how many micro models to place at each pressure node.

For example, the execution command unit 210 calculates a micro-model vessel capacity per unit volume, $\rho_k$, at myocardial node k, assuming that the micro models as a whole have a vessel capacity of 8% of the myocardial volume. The simulation condition determination unit 130 then determines the number $n_k$ of micro models to be connected to the pressure node k by using equation (1) as in the foregoing first embodiment.

The simulation condition determination unit 130 also determines other parameters according to user commands, which include the simulation time step size, termination conditions, and convergence conditions of analysis based on the Newton-Raphson method. The CAD system 100 then transmits the macro model, micro models, and simulation conditions to the managing node 200. In response, the managing node 200 submits jobs to a plurality of computing nodes to execute a coronary circulation simulation in a parallel processing environment.

(b) Equations Relating to Micro Model Vessels

The micro-model vessels are responsible for directly delivering oxygen and nutrition to the myocardium. With their volumetric changes, the vessels accumulate and discharge the blood repetitively. The coronary circulation simulation mimics not only transport of blood, but also such accumulation and discharge actions of the vessels as will be described below.

Generally, a vessel element has different diameters and different pressures at its opposite ends.

Figure 24:
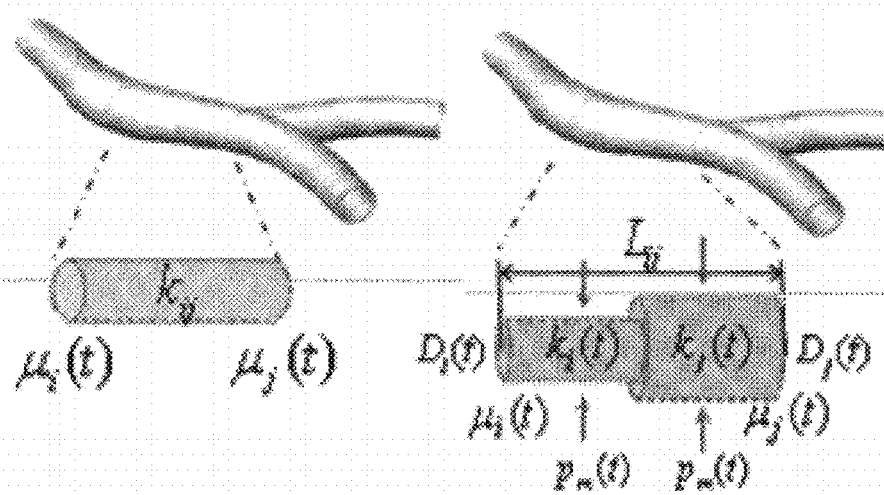
FIG. 24 illustrates a difference of vessel diameters.

FIG. 24 illustrates a difference of vessel diameters. In this illustrated model, the vessel element with a conductance of $k_{ij}$ is divided into two segments with respective conductances of $k_i(t)$ and $k_j(t)$. Suppose now that these two segments have constant inner pressures of $\mu_i(t)$ and $\mu_j(t)$. Then the vessel diameter $D_i(t)$ is determined from the difference between inner pressures (coronary blood pressure) and external pressure $p_m(t)$, as seen in the following equation (11). Here the external pressure means pressure of the surrounding myocardium and corresponds to the pressure value of a pressure node of myocardial finite elements.

$$D_i(t) = \alpha \cdot ((\mu_i(t) - p_m(t)) - (\mu_i^* - p_m^*)) + D_i^* \quad (11)$$

where $\alpha$ represents the elasticity of vessels, and * denotes a reference state.

For the sake of convenience, values obtained from the Hagen-Poiseuille flow are used to substitute for the conductance k of segments. The following equation (12) then gives the conductance $k_{ij}(t)$ of a vessel element as a harmony mean of $k_i(t)$ and $k_j(t)$ representing conductances of its segments.

$$k_{ij}(t) = \frac{k_i(t) \cdot k_j(t)}{k_i(t) + k_j(t)} = \frac{\pi}{64 \, \mu L_{ij}} \frac{D_i(t)^4 D_j(t)^4}{D_i(t)^4 + D_j(t)^4} \quad (12)$$

The amount of blood accumulated into segments of a vessel element is represented as a time derivative of its volume (as in the second term of equation (13)). At a vessel node i in the macro model, the flow rate conservation law holds as follows.

$$\sum_{j \in F_i} k_{ij}(t)(\mu_i) - (\mu_j) + \sum_{j \in F_i} \frac{\pi L_{ij}}{8} \frac{d(D_i(t)^2)}{dt} = 0 \quad (13)$$

(c) Basic Equations Representing Mixture of Cardiac FEM Model and Blood

The motion of a mixed body of myocardium and blood in the microcirculatory system is given by the following equation (14).

$$\rho a = \nabla \cdot (\sigma^s - pI) \quad (14)$$

where p represents inner pressure of myocardium, $\rho$ is density of the mixed body, a represents acceleration, and $\sigma^s$ is Cauchy stress tensor. The volume conservation law of the mixed body is given by the following equation (15) using volumetric change rate J.

$$(J - 1) - n \Delta V_{micro} = 0 \quad (15)$$

The second term of equation (15) represents volumetric changes in the micro models, indicating that the volume of the mixed body increases as much as the micro models accumulate more blood. $\Delta V_{Micro}$ represents the increase of volume per micro model, relative to the initial state, and n is the number of micro models contained in a unit myocardium volume.

There are five unknowns in the above set of equations, three for displacement components of the myocardium, one for myocardial pressure, and one for vessel pressure. The relationships among these unknown variables are expressed as:

$$\begin{pmatrix} A_{mic} & C^T & & K^T \\ C & B_{mac} & & H^T \\ & & D & G^T \\ K & H & G & F \end{pmatrix} \begin{pmatrix} \Delta \mu_{mic} \\ \Delta \mu_{mac} \\ \Delta u \\ \Delta p \end{pmatrix} = r \quad (16)$$

$A_{mic}$: micro model matrix
$B_{mac}$: macro model matrix
C: interaction between micro model and macro model
D: matrix relating to displacement of myocardium and fluid nodes
F: matrix relating to pressure in myocardium and fluid nodes
K: interaction of pressure between micro model and myocardial nodes
H: interaction of pressure between macro model and fluid nodes
$\Delta \mu_{mic}$: vector relating to pressure at micro model nodes
$\Delta \mu_{mac}$: vector relating to pressure at macro model nodes
$\Delta u$: vector relating to displacement of myocardium and fluid nodes
$\Delta p$: vector relating to pressure of myocardium and fluid nodes
r: residual vector The above-noted unknowns can be obtained by solving this matrix equation (16).

(d) Simulation Procedure

The computing nodes 400, 500, 600, . . . run in parallel to execute a coronary circulation simulation in accordance with commands from the execution command unit 210 in the managing node 200. This parallel process may use, for example, the Message-Passing Interface (MPI) standard. The execution command unit 210 assigns a process to one processor core to execute macro model computation. With this process (referred to as "macro procs"), the processor core acts as the macro analysis unit 450 discussed in FIG. 11.

The execution command unit 210 then assigns more processes to other processor cores to execute micro model computation. Also provided to these processor cores are parameters specifying, for example, which micro models to execute and which pressure nodes to connect micro models. The assigned processes (referred to as "micro procs") cause the processor cores to function as the micro analysis units 510, 520, . . . discussed in FIG. 11.

The execution command unit 210 further assigns yet another process to a processor core to control the entire procedure of a simulation. This processor core functions as the simulation control unit 440 discussed in FIG. 11. Alternatively, the functions of the simulation control unit 440 may be executed together with the macro process by the processor core serving as the macro analysis unit 450.

Figure 25:
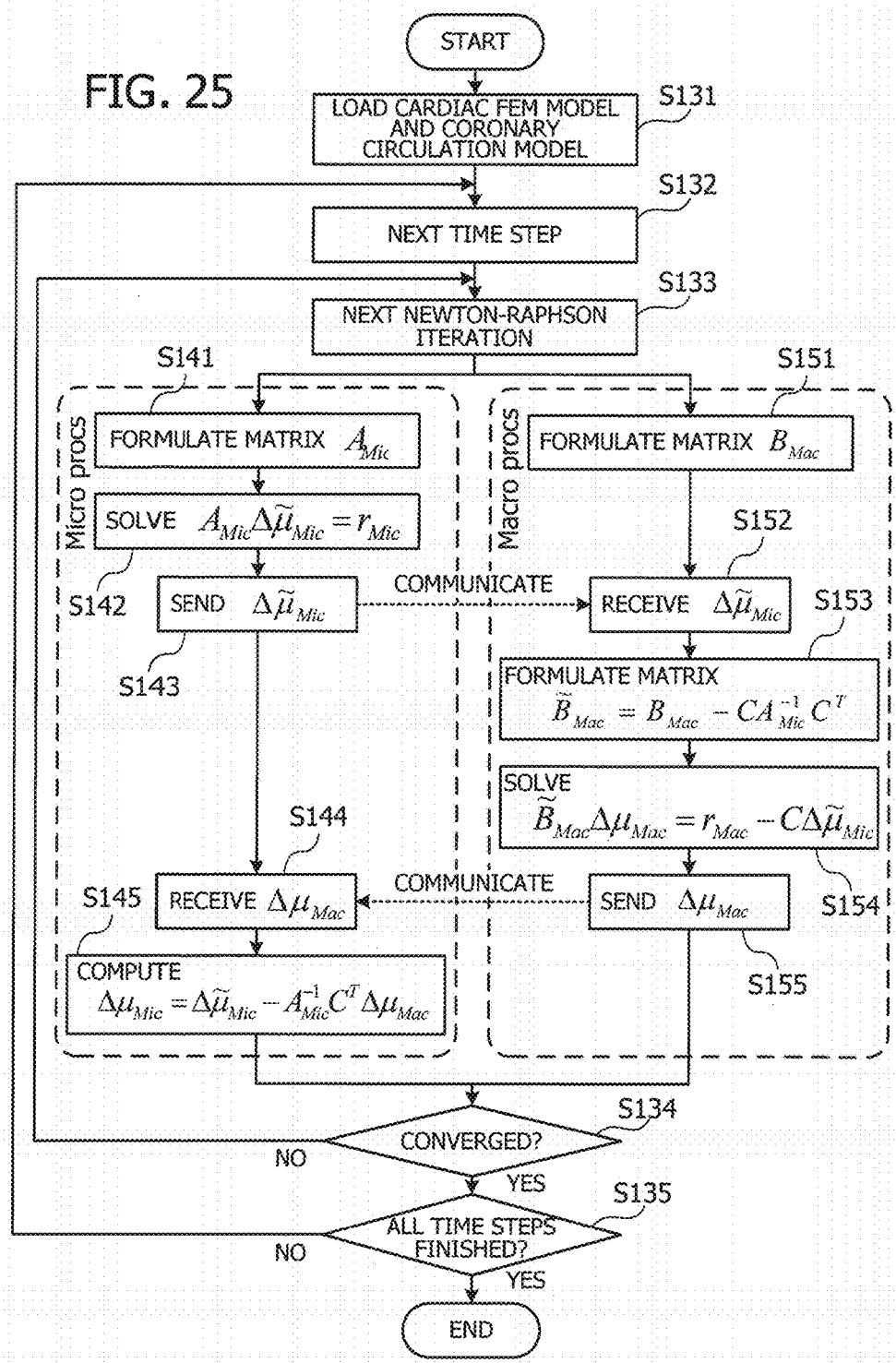
FIG. 25 is a flowchart illustrating an exemplary procedure of a coronary circulation simulation.

FIG. 25 is a flowchart illustrating an exemplary procedure of a coronary circulation simulation. Steps S131 to S135 in FIG. 25 are executed by the simulation control unit 440 to control the entire flow. Steps S141 to S145 are a micro process executed by the micro analysis units 510, 520, and so on. Steps S151 to S155 are a macro process executed by the macro analysis unit 450. The macro process includes analysis of contraction and relaxation of the myocardium, as well as the discharging of intracardiac blood.

This section will describe the entire flow control, micro process, and macro process individually, according to the step numbers seen in FIG. 25. First, the entire flow of the simulation process is controlled as follows:

(Step S131) The simulation control unit 440 causes each computing node 400, 500, 600, . . . to load a finite element model 310 and coronary circulation model (macro model 320 and micro model 330) of a heart from the storage device 300. The computing nodes 400, 500, 600, . . . store the loaded data in their local memory.

(Step S132) The simulation control unit 440 advances the time step of the simulation by one unit increment.

(Step S133) The simulation control unit 440 advances iteration cycles of the Newton-Raphson method for nonlinear analysis. For example, the simulation control unit 440 sends a command to the macro analysis unit 450 and micro analysis units 510, 520, . . . to execute the next Newton-Raphson iteration cycle. This command causes the individual micro analysis units 510, 520, . . . to work in parallel to execute steps S141 to S145, as well as the macro analysis unit 450 to execute steps S151 to S155.

(Step S134) The simulation control unit 440 determines whether the nonlinear analysis with the Newton-Raphson method has converged. This determination may be made by, for example, comparing a new analysis result with the previous one. If their difference is smaller than or equal to a specified threshold, the simulation control unit 440 determines that the solution has been converged and advances the process to step S135. If not, the simulation control unit 440 moves back to step S133 for the next iteration.

(Step S134) The simulation control unit 440 determines whether the computation has been finished for all time steps of the simulation. The simulation control unit 440 closes the coronary circulation simulation if it is found that every time step has been done. Otherwise, the simulation control unit 440 goes back to step S132.

These steps controls the entire process flow of coronary circulation simulation. During the above course, the micro analysis units 510, 520, . . . execute the following step S141 to S145 for a micro process.

(Step S141) Each of the micro analysis units 510, 520, . . . is associated with a micro model attached to a particular pressure node. The micro analysis units 510, 520, . . . formulate a micro model matrix $A_{Mic}$ for their corresponding pressure nodes.

(Step S142) Based on their respective matrices $A_{Mic}$ of step S141, the micro analysis units 510, 520, . . . calculate $\Delta\tilde{\mu}_{Mic}$ (with a tilde on top of $\mu$) according to equation (5).

(Step S143) Each micro analysis unit 510, 520, . . . sends the calculation result $\Delta\tilde{\mu}_{Mic}$ (with a tilde on top of $\mu$) of step S143 to the macro analysis unit 450.

(Step S144) The micro analysis units 510, 520, . . . receive from the macro analysis unit 450 a pressure increment $\Delta\mu_{Mac}$ of their corresponding pressure nodes.

(Step S145) Each micro analysis unit 510, 520, . . . calculates $\Delta\mu_{Mic}$ according to equation (7), using their respective pressure increment values received at step S144.

The above steps are executed for each micro model by the micro analysis units 510 operating in parallel. The macro analysis unit 450, on the other hand, executes macro process steps S151 to S155 as follows.

(Step S151) The macro analysis unit 450 formulates a macro model matrix $B_{Mac}$.

(Step S152) The macro analysis unit 450 receives $\Delta\tilde{\mu}_{Mic}$ (with a tilde on top of $\mu$) from each micro analysis unit 510, 520, and so on.

(Step S153) The macro analysis unit 450 formulates $\tilde{B}_{Mac}$ (with a tilde on top of B) defined in equation (4).

(Step S154) Based on equation (6), the macro analysis unit 450 calculates $\Delta\mu_{Mac}$ at each pressure node.

(Step S155) The macro analysis unit 450 sends $\Delta\mu_{Mac}$ to the micro analysis units 510, 520, . . . , depending on to which pressure node their respective micro models are connected.

These processing operations of FIG. 25 may be presented in a simplified way. That is, the simulation control unit 440 first reads a finite element model and coronary circulation model as input data for cardiac simulation. Then at each time step, the macro analysis unit 450 and micro analysis units 510, 520, . . . perform iterative calculation of the Newton-Raphson method for nonlinear analysis. Specifically, the macro analysis unit 450 first formulates a matrix $B_{Mac}$, while the micro analysis units 510, 520, . . . formulate their respective matrices $A_{Mic}$ and solve the equation formed from $A_{Mic}$. The micro analysis units 510, 520, . . . send their calculation results $\Delta\tilde{\mu}_{Mic}$ (with a tilde on top of $\mu$) to the macro analysis unit 450. The macro analysis unit 450 then calculates $\tilde{B}_{Mac}$ (with a tilde on top of B) and solve its equation. The macro analysis unit 450 supplies the micro analysis units 510, 520, . . . with $\Delta\mu_{Mac}$ for their calculation of $\Delta\mu_{Mic}$.

As can be seen from the above, the second embodiment is configured to execute parallel calculation of micro models by assigning a micro process to a plurality of CPU cores serving as micro analysis units 510. The second embodiment enables concurrent execution of the micro and macro processes at least in part and thus permits the parallel computing system to exert its performance. The second embodiment also takes advantage of a symmetric model, which reduces the data size of micro models by the factor of 128 compared with the case without symmetry.

The efficient use of a parallel computing system contributes to realization of a coronary circulation simulation that mimics even a blood flow in cardiac capillaries. This feature of the second embodiment makes it possible to investigate the behavior of a heart in its microcirculatory system, as opposed to conventional simulation methods. The scope of the simulation may be expanded to include delivery of chemical compounds and interaction between capillaries and muscle tissue. This expansion helps researchers to estimate possible effects or side effects of a new drug in development.

(C) Third Embodiment

This section describes a third embodiment which combines another type of simulation with the blood flow simulation of the first or second embodiment. This additional simulation enables analysis of metabolism of myocardial cells. Metabolism is a series of chemical reactions in which the myocardial cells produce adenosine triphosphate (ATP) from oxygen and nutrition obtained from the capillary blood flow. For mathematical modeling of metabolism, see the fifth non-patent document. The combined simulation of blood flow and myocardial metabolism only becomes possible with the proposed capillary-level blood flow simulation.

To implement a simulation for analyzing metabolism of myocardial cells, the third embodiment uses two additional equations (17) and (18), together with the foregoing equations discussed in the first or second embodiment.

$$\frac{\partial C}{\partial t} = -v \frac{\partial C}{\partial x} - \nabla \cdot D \nabla C \qquad (17)$$

Equation (17) describes the concentration C of oxygen and nutrition delivered by the coronary blood flow, where v is the blood velocity and D represents diffusion coefficients.

$$\frac{\partial C}{\partial t} = -\nabla \cdot K \nabla C + q \qquad (18)$$

where C is the concentration of oxygen and nutrients, K represents diffusion coefficients, and q indicates metabolic consumption of oxygen and nutrients by the myocardial cells. Equation (18) describes movement of oxygen and nutrition which is caused by the difference in concentration between the blood and myocardial cells.

The third embodiment solves the given equations including (17) and (18) by using the same method discussed in the first or second embodiment. Equation (17) applies to both the macro model and micro models. Equation (18) applies to myocardial finite elements having a micro model and a myocardial pressure node connecting that micro model. In this way, the third embodiment enables simulation of blood flow in combination with the metabolism of myocardial cells.

(D) Fourth Embodiment

This section describes a fourth embodiment which proposes a method for reducing the amount of computation relative to the foregoing third embodiment.

The metabolism is affected by the coronary blood flow, but its changes may not come to the surface until the heart beats ten or more times. The parallel computer may, however, consume a lot of time for computation of these ten heartbeats, depending on the performance of the parallel computer used. The fourth embodiment is thus directed to reduction of computational load in cardiac simulation. The second and fourth embodiments use the same system configuration discussed previously in FIGS. 8 to 11. Accordingly this section describes the fourth embodiment by using the same components illustrated in FIGS. 8 to 11.

Figure 26:
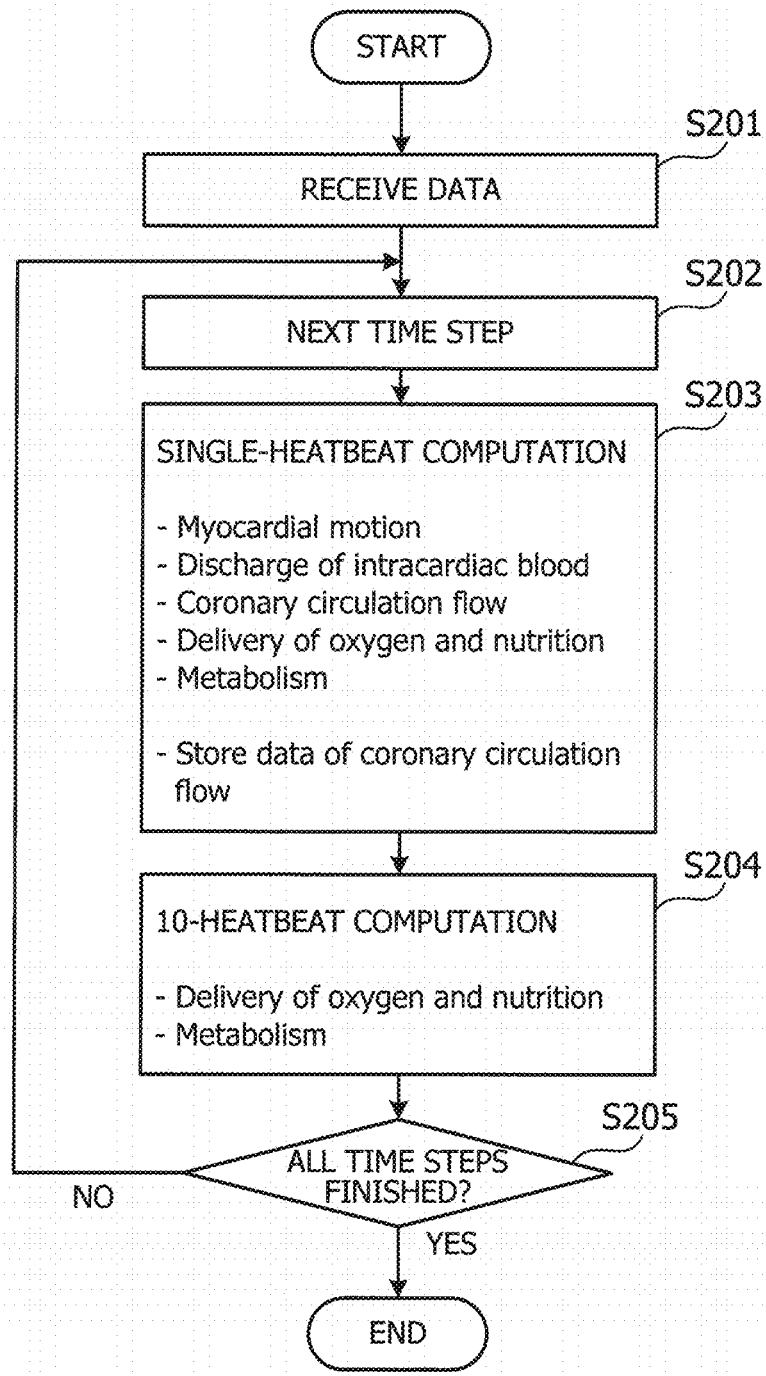
FIG. 26 is a flowchart illustrating an exemplary simulation procedure according to a fourth embodiment.

FIG. 26 is a flowchart illustrating an exemplary simulation procedure according to the fourth embodiment. Each operation in FIG. 26 is described below in the order of step numbers.

(Step S201) The simulation control unit 440 causes each computing node 400, 500, 600, . . . to load input data from the storage device 300, including a finite element model 310 and coronary circulation model (macro model 320 and micro model 330) of a heart, as well as data for analysis of metabolism of myocardial cells. The computing nodes 400, 500, 600, . . . store the loaded data in their local memory.

(Step S202) The simulation control unit 440 advances the time step of the simulation by one unit increment.

(Step S203) The macro analysis unit 450 works in cooperation with the micro analysis units 510, 520, . . . to simulate one heartbeat. Calculated at this step S203 are motion of the myocardium, discharging of intracardiac blood, flow of coronary circulation, delivery of oxygen and nutrition, and metabolism. The macro analysis unit 450 and the micro analysis units 510, 520, . . . store the resulting data of coronary circulation flow in their respective local memory.

(Step S204) The macro analysis unit 450 works in cooperation with the micro analysis units 510, 520, . . . to simulate ten heartbeats. Calculated at this step S204 are delivery of oxygen and nutrition and metabolism.

(Step S205) The simulation control unit 440 determines whether the computation has been finished for all time steps of the simulation. The simulation control unit 440 closes the coronary circulation simulation if it is found that every time step has been done. Otherwise, the simulation control unit 440 goes back to step S202.

As can be seen from the above steps, the proposed method of the fourth embodiment first simulates a single heartbeat to analyze the motion of myocardium, discharging of intracardiac blood, flow of coronary circulation, delivery of oxygen and nutrition, and metabolism. At each time step in this single heartbeat duration, the obtained data of flow rates in the coronary circulation is saved. Then with the saved flow rate data, the proposed method executes computation of ten more heartbeats, now focusing on the delivery of oxygen and nutrients and the metabolism. In this way, the proposed method reduces the amount of computational load in simulating ten or more heartbeats and thus enables the user to analyze possible variations in the metabolism in a practical simulation time, without the need for a faster parallel computer.

(E) Fifth Embodiment

This section describes a fifth embodiment which uses features of the first to fourth embodiments to evaluate effects of coronary artery stenosis.

Figure 27:
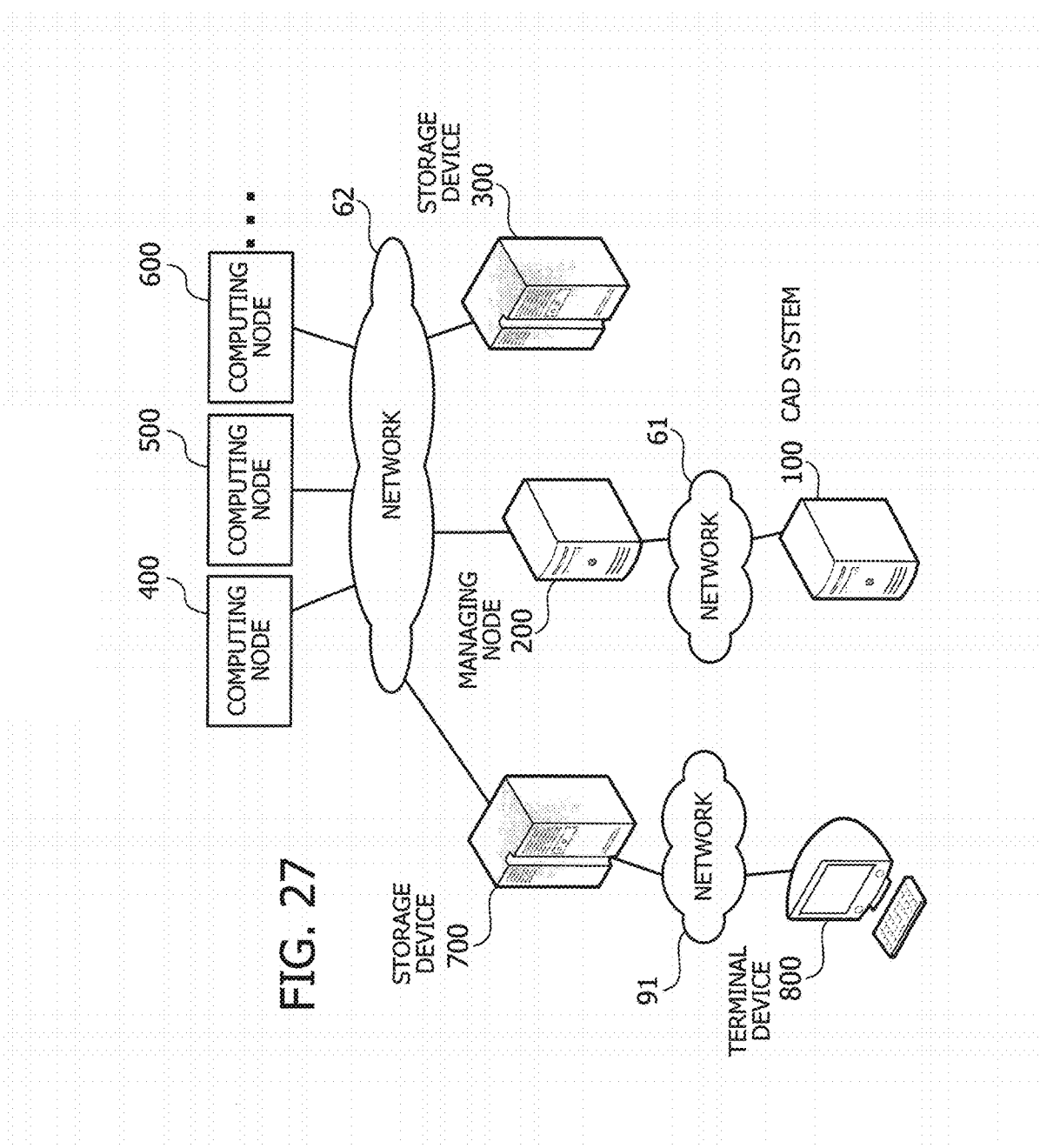
FIG. 27 illustrates an exemplary system configuration according to a fifth embodiment.

FIG. 27 illustrates an exemplary system configuration according to the fifth embodiment. This section will focus on its distinct features, while affixing like reference numerals to like elements discussed in the second embodiment. Besides having the same system elements of the second embodiment in FIG. 8, the fifth embodiment in FIG. 27 further includes a storage device 700, a network 91, and a terminal device 800.

The additional storage device 700 is linked to one network 62 for use by the computing nodes 400, 500, 600, . . . to save data of their analysis results. The storage device 700 is also accessible to a remote terminal device 800 via another network 91. This terminal device 800 is used to evaluate the effect of coronary artery stenosis based on the analysis results stored in the storage device 700.

For example, the user produces data of a coronary circulation model by using a CAD system 100 from medical images obtained from a Computed Tomography (CT) or Magnetic Resonance Imaging (MRI) system (not illustrated). This coronary circulation model reflects some constricted portions of the patient's coronary arteries. Or the produced coronary circulation model may have a couple of arteries with some amount of stenosis that is set by the user to represent a future risk of narrowing or blockage of the coronary arteries.

With the model data produced above, a plurality of computing nodes 400, 500, 600, simulate the coronary circulation according to the foregoing first to fourth embodiments. The user can receive the result from the simulation system via his or her terminal device 800. The terminal device 800 executes evaluation of the analysis result in terms of how the stenosis of coronary arteries affects the motion of the myocardium, discharging of intracardiac blood, flow of coronary circulation, delivery of oxygen and nutrition, and metabolism of the heart in question.

(F) Other Embodiments and Variations

The first to fifth embodiments have been described above in the context of coronary circulation simulation. The proposed simulation method may similarly be applied to hemodynamics simulation of other organs.

The system according to the second to fifth embodiments has also been described as being formed from a plurality of apparatuses. It is possible, however, to integrate any two or more of those apparatuses into a single apparatus. For example, the foregoing CAD system 100 and managing node 200 may be implemented in a single computer.

The data processing operations of the second to fifth embodiment are encoded in software programs for execution by CPU cores. The programmed code may partly be implemented in the form of electronic circuit. For example, a part of the foregoing processing functions may be implemented by using one or more digital signal processors (DSP), application specific integrated circuits (ASIC), programmable logic devices (PLD), and the like.

Various embodiments and their variations have been described above. According to one aspect of the embodiments, the proposed method and apparatus efficiently simulate the dynamics of blood circulation, including all or some of the capillary-level analysis of blood pressure drop, evaluation of a heart with a particular microcirculation structure, and combined analysis of metabolism and microcirculation.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A coronary circulation simulation method executed by a first processor and a plurality of second processors, each of the first and the second processors being coupled to a storage device, the coronary circulation simulation method comprising:
   storing a geometric model representing a shape of a heart as a collection of elements formed from a plurality of nodes and a plurality of connections among the nodes in the storage device;
   receiving a first vessel network model representing a network of first vessels whose diameters are larger than or equal to a specified threshold, wherein the first vessel network model is a macro model;
   storing the first vessel network model in the storage device;
   receiving a plurality of second vessel network models each representing a network of second vessels whose diameters are smaller than the specified threshold, the plurality of second vessel network models being independent of each other, wherein one or more of the second vessel network models are connected to each of the nodes, wherein the second vessel network models are micro models;
   storing the plurality of second vessel network models in the storage device;
   first analyzing, by the first processor, first hemodynamics in the first vessels belonging to the first vessel network model, based on the geometric model of the heart;
   second analyzing, by the plurality of second processors in parallel without interactions, second hemodynamics in the second vessels belonging to the second vessel network models connected to the plurality of nodes, by using blood pressure data in the first vessels at the nodes, the blood pressure data being included in result data of the first analyzing which indicates the first hemodynamics in the first vessels at each of the nodes; and
   outputting the first hemodynamics in the first vessels and the second hemodynamics in the second vessels,
   wherein:
      the first analyzing and the second analyzing include analyzing the first and the second hemodynamics in the first and second vessels reflecting motion of the heart by using a Newton-Raphson method for non-linear analysis, and are performed alternately;
      the second analyzing includes calculating tentative blood pressure increments in the second vessel network models by using an equation from which first blood pressure increments in the first vessel network model have been eliminated;
      the first analyzing includes calculating the first blood pressure increments in the first vessel network model by using the tentative blood pressure increments in the second vessel network models; and
      the second analyzing includes calculating second blood pressure increments in the second vessel network models by using the first blood pressure increments in the first vessel network model.

2. The coronary circulation simulation method according to claim 1, wherein:
   the second vessel network model includes capillaries and intermediate-layer vessels placed at opposite ends of the capillaries to connect the capillaries with the first vessels defined in the first vessel network model; and
   the intermediate-layer vessels are divided into arterial vessels and venous vessels which are symmetrically arranged with respect to the capillaries.

3. The coronary circulation simulation method according to claim 1, wherein a larger number of second vessel network models are connected to a node with a higher vessel density, so as to reflect an anatomical feature of the heart.

4. The coronary circulation simulation method according to claim 1, wherein a larger number of second vessel network models are placed at the nodes on an endocardial side of a wall of the heart than at the nodes on an epicardial side of the wall of the heart.

5. A coronary circulation simulator apparatus comprising:
   a storage device;
   a first processor and a plurality of second processors configured to perform a procedure, each of the first and the second processors being coupled to the storage device, the procedure including:
      storing a geometric model representing a shape of a heart as a collection of elements formed from a plurality of nodes and a plurality of connections among the nodes in the storage device;
      receiving a first vessel network model representing a network of first vessels whose diameters are larger than or equal to a specified threshold, wherein the first vessel network model is a macro model;
      storing the first vessel network model in the storage device;
      receiving a plurality of second vessel network models each representing a network of second vessels whose diameters are smaller than the specified threshold, the plurality of second vessel network models being independent of each other, wherein one or more of the second vessel network models are connected to each of the nodes, wherein the second vessel network models are micro models;
      storing the plurality of second vessel network models in the storage device;

first analyzing, by the first processor, first hemodynamics in the first vessels belonging to the first vessel network model, based on the geometric model of the heart; and second analyzing, by the plurality of second processors in parallel without interactions, second hemodynamics in the second vessels belonging to the second vessel network models connected to the plurality of nodes, by using blood pressure data in the first vessels at the nodes, the blood pressure data being included in result data of the first analyzing which indicates the first hemodynamics in the first vessels at each of the nodes; and outputting the first hemodynamics in the first vessels and the second hemodynamics in the second vessels, wherein:

the first analyzing and the second analyzing include analyzing the first and the second hemodynamics in the first and second vessels reflecting motion of the heart by using a Newton-Raphson method for non-linear analysis, and are performed alternately;

the second analyzing includes calculating tentative blood pressure increments in the second vessel network models by using an equation from which first blood pressure increments in the first vessel network model have been eliminated;

the first analyzing includes calculating the first blood pressure increments in the first vessel network model by using the tentative blood pressure increments in the second vessel network models; and the second analyzing includes calculating second blood pressure increments in the second vessel network models by using the first blood pressure increments in the first vessel network model.

6. A non-transitory computer-readable medium storing a program for execution by a computer including a first processor and a plurality of second processors , each of the first and the second processors being coupled to a storage device, the program causing the computer to perform a procedure comprising:

storing a geometric model representing a shape of a heart as a collection of elements formed from a plurality of nodes and a plurality of connections among the nodes in the storage device;

receiving a first vessel network model representing a network of first vessels whose diameters are larger than or equal to a specified threshold, wherein the first vessel network model is a macro model;

storing the first vessel network model in the storage device;

receiving a plurality of second vessel network models each representing a network of second vessels whose diameters are smaller than the specified threshold, the plurality of second vessel network models being independent of each other, wherein one or more of the second vessel network models are connected to each of the nodes, wherein the second vessel network models are micro models;

storing the plurality of second vessel network models in the storage device;

first analyzing, by the first processor, first hemodynamics in the first vessels belonging to the first vessel network model, based on the geometric model of the heart;

second analyzing, by the plurality of second processors in parallel without interactions, second hemodynamics in the second vessels belonging to the second vessel network models connected to the plurality of nodes, by using blood pressure data in the first vessels at the nodes, the blood pressure data being included in result data of the first analyzing which indicates the first hemodynamics in the first vessels at each of the nodes; and outputting the first hemodynamics in the first vessels and the second hemodynamics in the second vessels, wherein:

the first analyzing and the second analyzing include analyzing the first and the second hemodynamics in the first and second vessels reflecting motion of the heart by using a Newton-Raphson method for non-linear analysis, and are performed alternately;

the second analyzing includes calculating tentative blood pressure increments in the second vessel network models by using an equation from which first blood pressure increments in the first vessel network model have been eliminated;

the first analyzing includes calculating the first blood pressure increments in the first vessel network model by using the tentative blood pressure increments in the second vessel network models; and the second analyzing includes calculating second blood pressure increments in the second vessel network model by using the first blood pressure increments in the first vessel network model.

\* \* \* \* \*